United States Patent
Gurevich et al.

(10) Patent No.: US 10,783,636 B2
(45) Date of Patent: *Sep. 22, 2020

(54) METHODS AND SYSTEMS FOR CHARACTERIZING TISSUE OF A SUBJECT

(71) Applicant: Stryker European Operations Limited, Carrigtwohill (IE)

(72) Inventors: Lina Gurevich, Vancouver (CA); Jorgen Walle-Jensen, Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 101 days.

This patent is subject to a terminal disclaimer.

(21) Appl. No.: 15/855,587

(22) Filed: Dec. 27, 2017

(65) Prior Publication Data
US 2018/0158187 A1   Jun. 7, 2018

Related U.S. Application Data

(63) Continuation of application No. 15/013,945, filed on Feb. 2, 2016, now Pat. No. 9,892,513.
(Continued)

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0071* (2013.01); *A61B 5/445* (2013.01);
(Continued)

(58) Field of Classification Search
CPC ......... G06T 7/0016; G06T 2207/30088; G06T 2207/10064; G06T 2207/30104;
(Continued)

(56) References Cited

U.S. PATENT DOCUMENTS

| 8,488,863 B2 | 6/2013 | Boucheron |
| 9,892,513 B2 * | 2/2018 | Gurevich ............. A61B 5/0071 |

(Continued)

FOREIGN PATENT DOCUMENTS

| CN | 101313847 A | 12/2008 |
| CN | 101460090 A | 6/2009 |

(Continued)

OTHER PUBLICATIONS

European Partial Supplementary Search Report dated Feb. 25, 2020, for Patent Application No. 17833161.7, filed Jul. 28, 2017, thirteen pages.

(Continued)

*Primary Examiner* — Jon Chang
(74) *Attorney, Agent, or Firm* — Morrison & Foerster LLP

(57) ABSTRACT

Methods and systems for characterizing tissue of a subject are disclosed. The method includes receiving a time series of fluorescence images of the tissue of the subject wherein the images define a plurality of calculation regions, generating a plurality of time-intensity curves for the plurality of calculation regions, creating a set of parameter values for each calculation region, generating a total rank value for each calculation region by comparing the sets of parameter values, and converting the total rank value into a ranking map image. Also disclosed are methods and systems for characterizing a wound in tissue by generating a wound index value.

24 Claims, 15 Drawing Sheets
(7 of 15 Drawing Sheet(s) Filed in Color)

Related U.S. Application Data

(60) Provisional application No. 62/110,609, filed on Feb. 2, 2015, provisional application No. 62/174,225, filed on Jun. 11, 2015.

(51) Int. Cl.
    *G16H 50/50*     (2018.01)
    *A61B 6/00*     (2006.01)

(52) U.S. Cl.
    CPC .............. *G16H 50/50* (2018.01); *A61B 6/486* (2013.01); *A61B 6/507* (2013.01); *A61B 6/5217* (2013.01); *A61B 2576/02* (2013.01); *G06T 2207/10064* (2013.01); *G06T 2207/30088* (2013.01); *G06T 2207/30096* (2013.01); *G06T 2207/30104* (2013.01); *G06T 2210/41* (2013.01); *G06T 2211/404* (2013.01)

(58) Field of Classification Search
    CPC ........... G06T 2210/41; G06T 2211/404; G06T 2207/30096; A61B 5/445; A61B 5/0071; A61B 2576/02; A61B 6/507; A61B 6/5217; A61B 6/486; G16H 50/50
    See application file for complete search history.

(56) References Cited

U.S. PATENT DOCUMENTS

| | | | |
|---|---|---|---|
| 10,026,159 | B2 | 7/2018 | Walle-Jensen et al. |
| 2001/0036304 | A1 | 11/2001 | Yang et al. |
| 2002/0183621 | A1* | 12/2002 | Pfeiffer ................ A61B 5/0059 600/473 |
| 2004/0013292 | A1 | 1/2004 | Raunig |
| 2005/0043614 | A1 | 2/2005 | Huizenga |
| 2006/0013454 | A1 | 1/2006 | Flewelling |
| 2006/0247514 | A1 | 11/2006 | Panasyuk |
| 2007/0016029 | A1 | 1/2007 | Donaldson et al. |
| 2008/0101678 | A1 | 5/2008 | Suliga et al. |
| 2008/0125643 | A1 | 5/2008 | Huisman et al. |
| 2009/0062876 | A1 | 3/2009 | Cohen |
| 2009/0097723 | A1 | 4/2009 | Washburn et al. |
| 2009/0252682 | A1 | 10/2009 | Hillman |
| 2009/0290017 | A1 | 11/2009 | Shibasaki |
| 2010/0215226 | A1 | 8/2010 | Kaufman et al. |
| 2011/0071403 | A1* | 3/2011 | Sevick-Muraca .... A61B 5/0059 600/476 |
| 2011/0208061 | A1* | 8/2011 | Chang ................... G06T 7/0016 600/458 |
| 2011/0311026 | A1 | 12/2011 | Lalena |
| 2012/0070044 | A1 | 3/2012 | Avinash et al. |
| 2012/0155735 | A1 | 6/2012 | Friedman |
| 2012/0214180 | A1 | 8/2012 | Hess et al. |
| 2013/0051651 | A1 | 2/2013 | Leary et al. |
| 2013/0096392 | A1 | 4/2013 | Adams |
| 2013/0195329 | A1 | 8/2013 | Canda et al. |
| 2013/0216482 | A1* | 8/2013 | Kwon .................. A61B 5/0071 424/9.6 |
| 2013/0345560 | A1* | 12/2013 | Ferguson, Jr. ....... A61B 5/0071 600/431 |
| 2014/0049555 | A1 | 2/2014 | Bzdusek et al. |
| 2015/0004630 | A1 | 1/2015 | Lange et al. |
| 2016/0253800 | A1 | 9/2016 | Gurevich |
| 2016/0290926 | A1 | 10/2016 | Notingher |
| 2016/0314585 | A1 | 10/2016 | Thomas |
| 2016/0350913 | A1* | 12/2016 | Nagae .................... A61B 6/487 |
| 2017/0071509 | A1 | 3/2017 | Pandey |
| 2017/0084012 | A1 | 3/2017 | Walle-Jensen et al. |
| 2017/0100037 | A1* | 4/2017 | Harmelin ............. A61B 5/0071 |
| 2018/0028079 | A1 | 2/2018 | Gurevich et al. |

FOREIGN PATENT DOCUMENTS

| | | |
|---|---|---|
| CN | 102209495 A | 10/2011 |
| CN | 103491874 A | 1/2014 |
| JP | 2001-104237 A | 4/2001 |
| JP | 2001-285858 A | 10/2001 |
| JP | 2001-525580 A | 12/2001 |
| JP | 2003-510121 A | 3/2003 |
| JP | 2005-342434 A | 12/2005 |
| JP | 2008-086670 A | 4/2008 |
| JP | 2008-535600 A | 9/2008 |
| JP | 2009-502270 A | 1/2009 |
| JP | 2009-279150 A | 12/2009 |
| JP | 2010-512900 A | 4/2010 |
| JP | 2011-042581 A | 3/2011 |
| JP | 2011-509789 A | 3/2011 |
| JP | 2011-519589 A | 7/2011 |
| JP | 2012-021002 A | 2/2012 |
| JP | 2012-508053 A | 4/2012 |
| JP | 2012-198139 A | 10/2012 |
| JP | 2012-523877 A | 10/2012 |
| JP | 2013-502263 A | 1/2013 |
| JP | 2013-510289 A | 3/2013 |
| JP | 2015-524329 A | 8/2015 |
| KR | 10-20110011655 A | 2/2011 |
| WO | WO-1999/028856 A1 | 6/1999 |
| WO | WO-2001/22870 A1 | 4/2001 |
| WO | WO 2006/123742 A1 | 11/2006 |
| WO | WO-2009/127972 A2 | 10/2009 |
| WO | 2010/119356 A2 | 10/2010 |
| WO | WO-2013/146841 A1 | 10/2013 |
| WO | WO-2013/190391 A2 | 12/2013 |
| WO | WO-2014/139021 A1 | 9/2014 |
| WO | WO-2015/001427 A2 | 1/2015 |
| WO | WO-2015/052710 A1 | 4/2015 |
| WO | 2016/069788 A1 | 5/2016 |
| WO | WO-2016/087589 A1 | 6/2016 |
| WO | WO-2016/123705 A1 | 8/2016 |
| WO | WO-2017/051230 A1 | 3/2017 |
| WO | WO-2018/018160 A1 | 2/2018 |

OTHER PUBLICATIONS

Japanese Office Action dated Feb. 10, 2020, for Patent Application No. 2018-556329, filed Jul. 28, 2017, nine pages.
U.S. Non Final Office Action dated Dec. 12, 2019, for U.S. Appl. No. 15/663,290, filed Jul. 28, 2017, ten pages.
Chinese Office Action dated Dec. 26, 2019, for Patent Application No. 201680020302.2, filed Feb. 2, 2016, thirty-five pages.
Australian Office Action dated Aug. 7, 2018 for Australian Patent Application No. 2016214922 filed on Jul. 27, 2017, two pages.
Canadian Office Action dated May 23, 2019 for CA Application No. 3,021,481, filed on Oct. 16. 2018, four pages.
Canadian Office Action dated Nov. 26, 2018 for CA Application No. 2,975,295, filed on Jul. 28, 2017, three pages.
Canadian Office Action dated Nov. 7, 2019 for CA Application No. 2,975,295, filed on Jul. 28, 2017, three pages.
European Office Action dated Oct. 2, 2018 for EP Application No. 16746031.0 filed on Aug. 22, 2017, nine pages.
European Search Report dated Sep. 12, 2018 for EP Application No. 16746031.0 filed on Aug. 22, 2017, four pages.
Gannot et al. (Nov. 11, 2004). "Fluorescence Imaging of Lesions, Deep Beneath Tissue Surface." 17th Annual Meeting of the IEEE Lasers and Electro-Optics Society, pp. 898-899.
Hui, F. et al. (Nov. 3, 2014). "Quantitative Spatial and Temporal Analysis of Fluorescein Angiography Dynamics in the Eye," Plos One 9(11):e111330, pp. 1-10.
Igari, K. et al. (Oct. 2013). "Quantitative Evaluation of the Outcomes of Revascularization Procedures for Peripheral Arterial Disease Using Indocyanine Green Angiography," *European Journal of Vascular and Endovascular Surgery* 46(4):460-465.
International Preliminary Report on Patentability dated Apr. 5, 2018, for PCT/IB2016/001214 filed on Jul. 29, 2016, seven pages.
International Preliminary Report on Patentability dated Aug. 17, 2017, for PCT/CA2016/050092 filed on Feb. 2, 2016, five pages.
International Preliminary Report on Patentability dated Aug. 24, 2017, for PCT/IB2016/00124 filed on Feb. 5, 2016, seven pages, (with English Translation).

(56) References Cited

OTHER PUBLICATIONS

International Preliminary Report on Patentability dated Feb. 7, 2019, for PCT Application No. PCT/CA2017/050912 filed on Jul. 28, 2017, eight pages.
International Search Report and Written Opinion dated Apr. 22, 2016 for PCT/IB2016/00124 filed on Feb. 5, 2016, eleven pages, (with English Translation).
International Search Report and Written Opinion dated May 5, 2016 for PCT/CA2016/050092 filed on Feb. 2, 2016, seven pages.
International Search report and Written Opinion dated Nov. 14, 2017, for PCT Application No. PCT/CA2017/050912 filed on Jul. 28, 2017, thirteen pages.
Invitation to Pay Additional Fees and, where Applicable, Protest Fee dated Oct. 5, 2017, for PCT Application No. PCT/CA2017/050912 filed on Jul. 28, 2017, two pages.
Japanese Notice of Allowance dated Mar. 26, 2019 for JP Application No. 2017-540738 filed on Aug. 1, 2017, 6 pages.
Japanese Office Action dated Nov. 2, 2018 for JP Application No. 2017-540738 filed on Aug. 1, 2017, 5 pages.
Korean Notice of Allowance dated Jul. 9, 2019 for KR Application No. 2017-7024707 filed on Sep. 1, 2017, three pages.
Korean Office Action dated Jan. 3, 2019 for KR Application No. 2017-7024707 filed on Sep. 1, 2017, six pages.
Lauer, G. et al. (Jul. 2000). "Expression and Proteolysis of Vascular Endothelial Growth Factor is Increased in Chronic Wounds, "Journal of Investigative Dermatology 115(1):12-18.
Leung, D.W. et al. (Dec. 8, 1989). "Vascular Endothelial Growth Factor is a Secreted Angiogenic Mitogen," Science 246:1306-1309.
U.S. Corrected Notice of Allowability dated May 23, 2018, for U.S. Appl. No. 15/224,342, filed Jul. 29, 2016, two pages.
U.S. Non Final Office Action dated Oct. 30, 2017, for U.S. Appl. No. 15/224,342, filed Jul. 29, 2016, sixteen pages.
U.S. Non-Final Office Action dated Aug. 24, 2017, for U.S. Appl. No. 15/013,945, filed Feb. 2, 2016, eight pahes.
U.S. Notice of Allowance dated Mar. 15, 2018, for U.S. Appl. No. 15/224,342, filed Jul. 29, 2016, eight pages.
U.S. Notice of Allowance dated Sep. 28, 2017, for U.S. Appl. No. 15/013,945, filed Feb. 2, 2016, eight pages.
U.S. Unpublished U.S. Appl. No. 15/224,088, filed Jul. 29, 2016 entitled, Methods and Systems for Assessing Healing of Tissue.
Wietecha, M.S. et al. (2013). "Mechanisms of Vessel Regression: Toward an Understanding of the Resolution of Angiogenesis," *Current Topics in Microbiology and Immunology* 367:3-32.

* cited by examiner

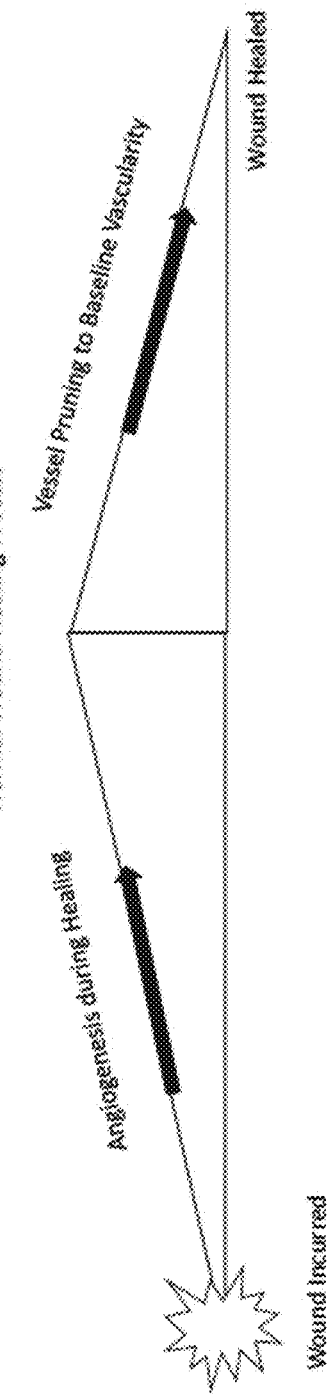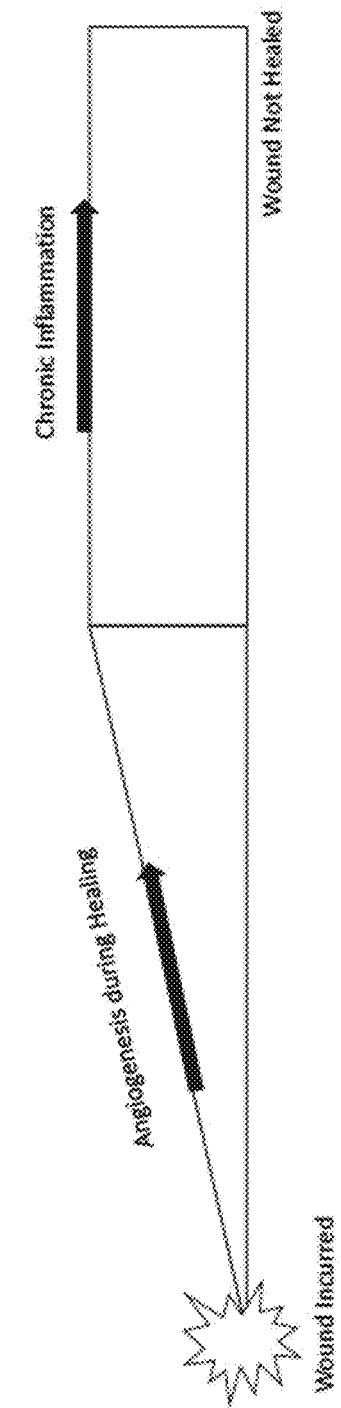
FIG. 5A
FIG. 5B

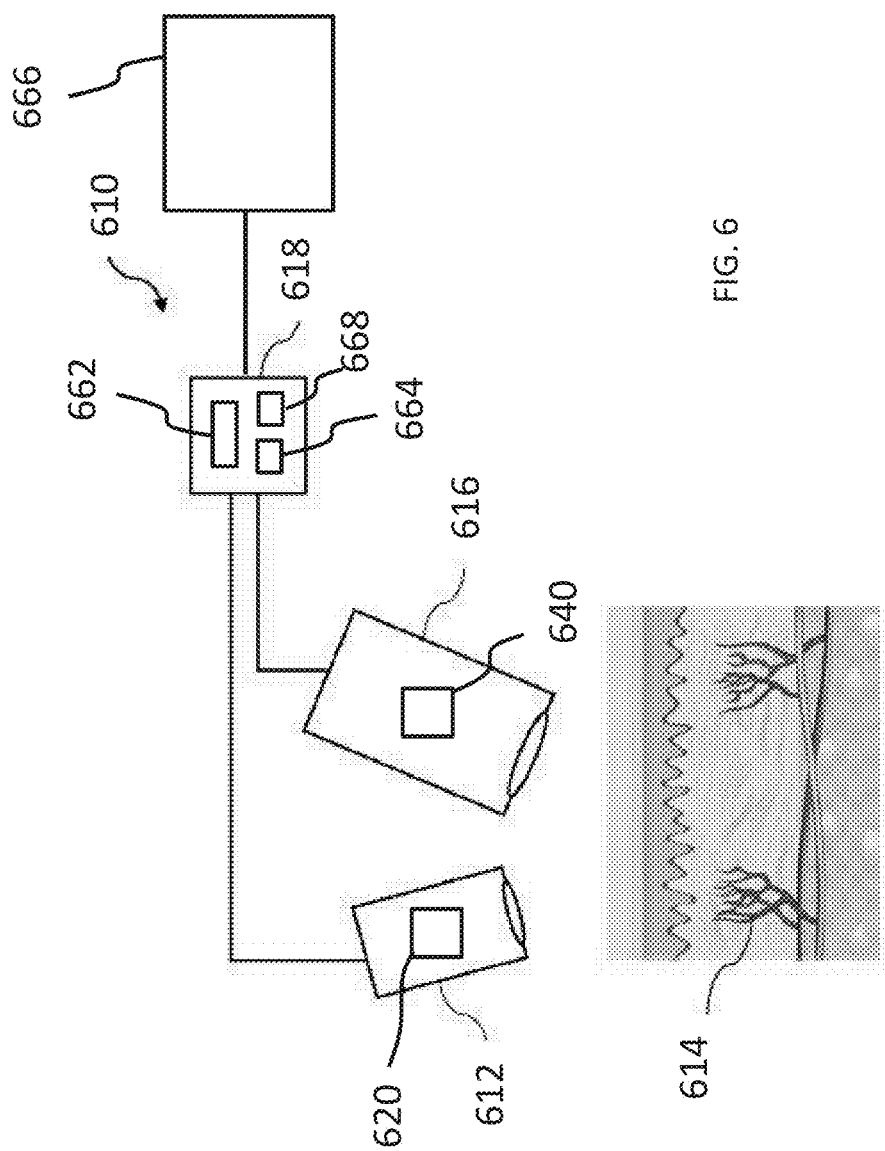

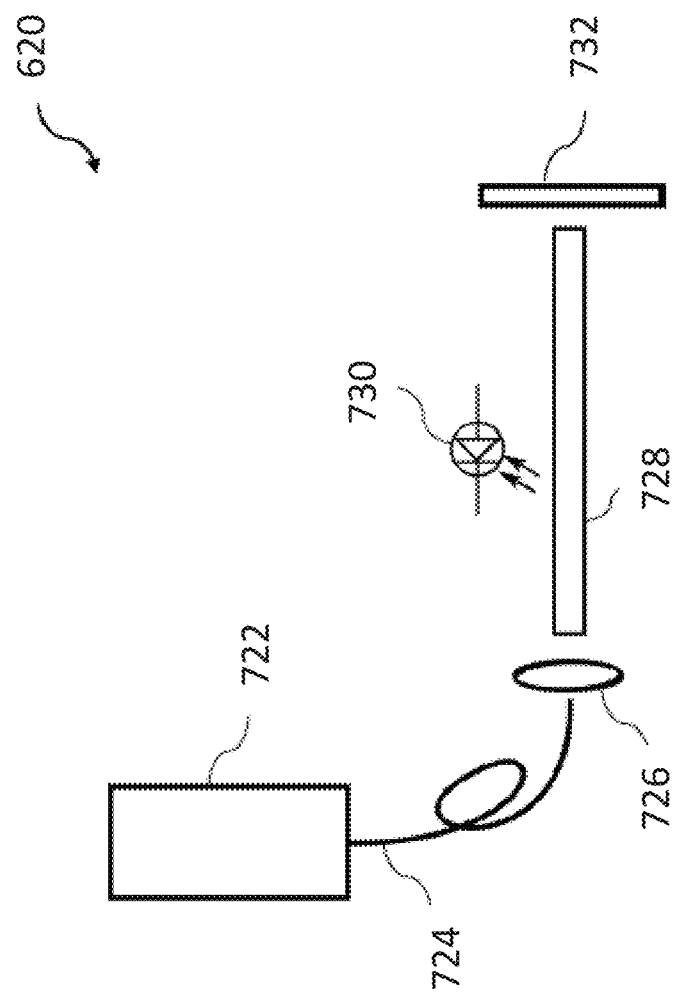

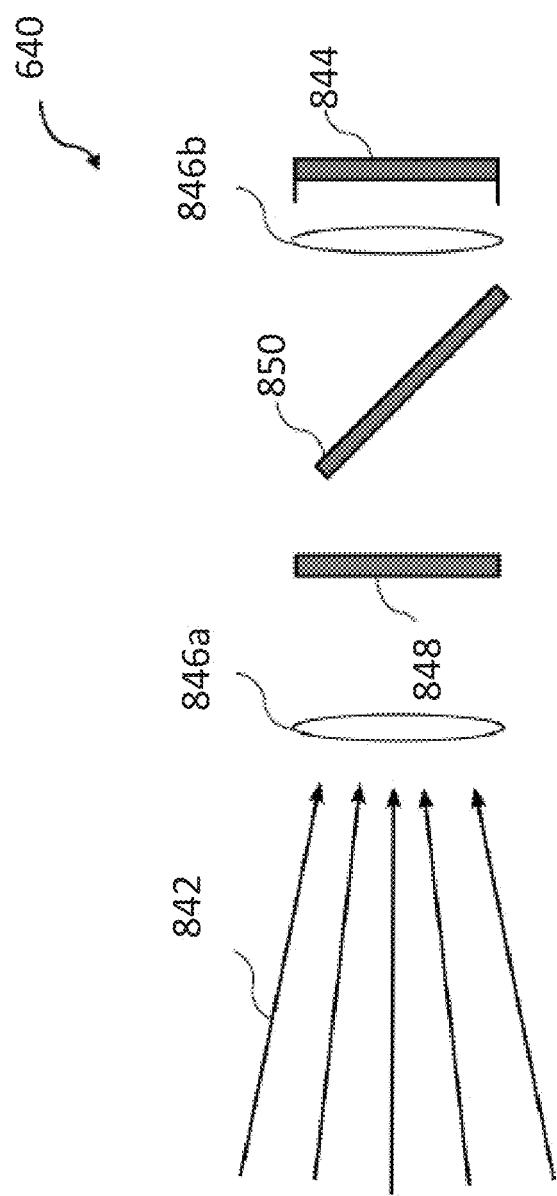

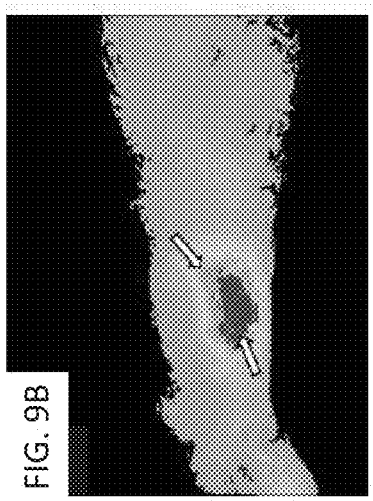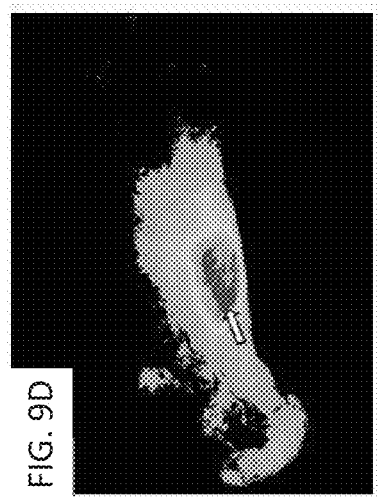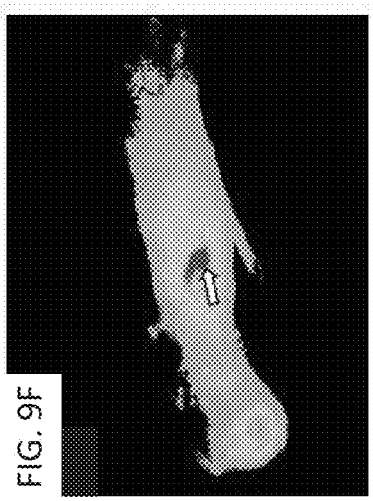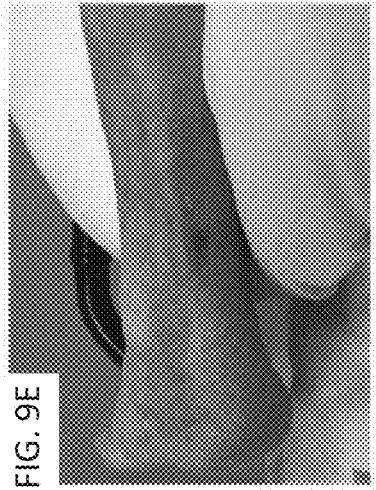

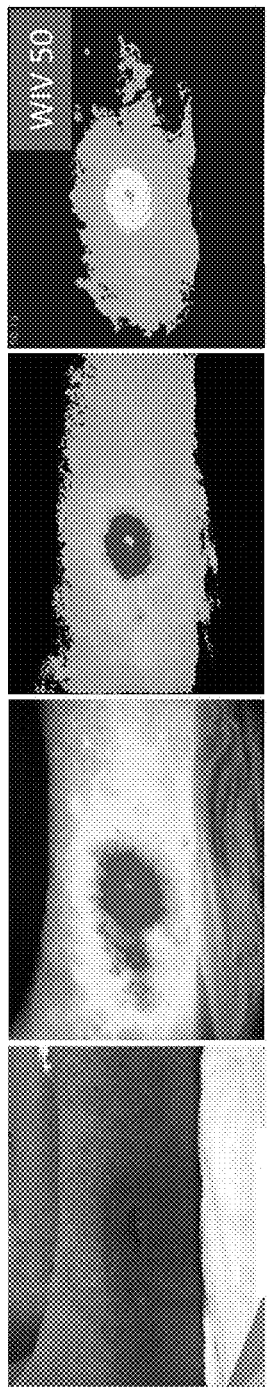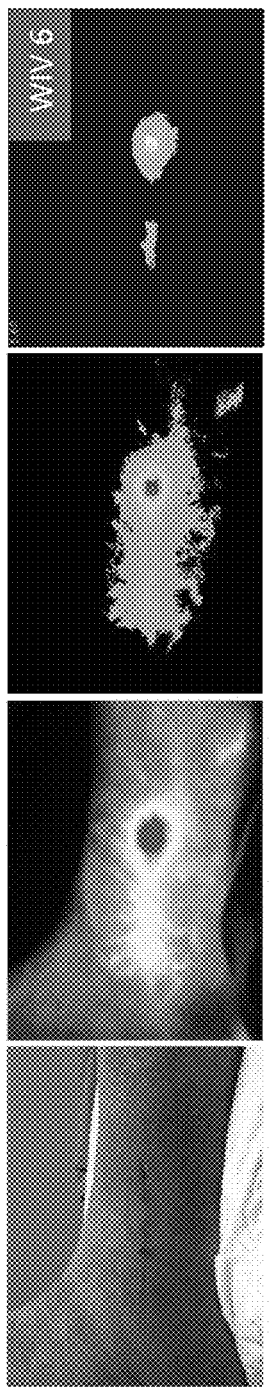

Intentionally left blank
Image not available

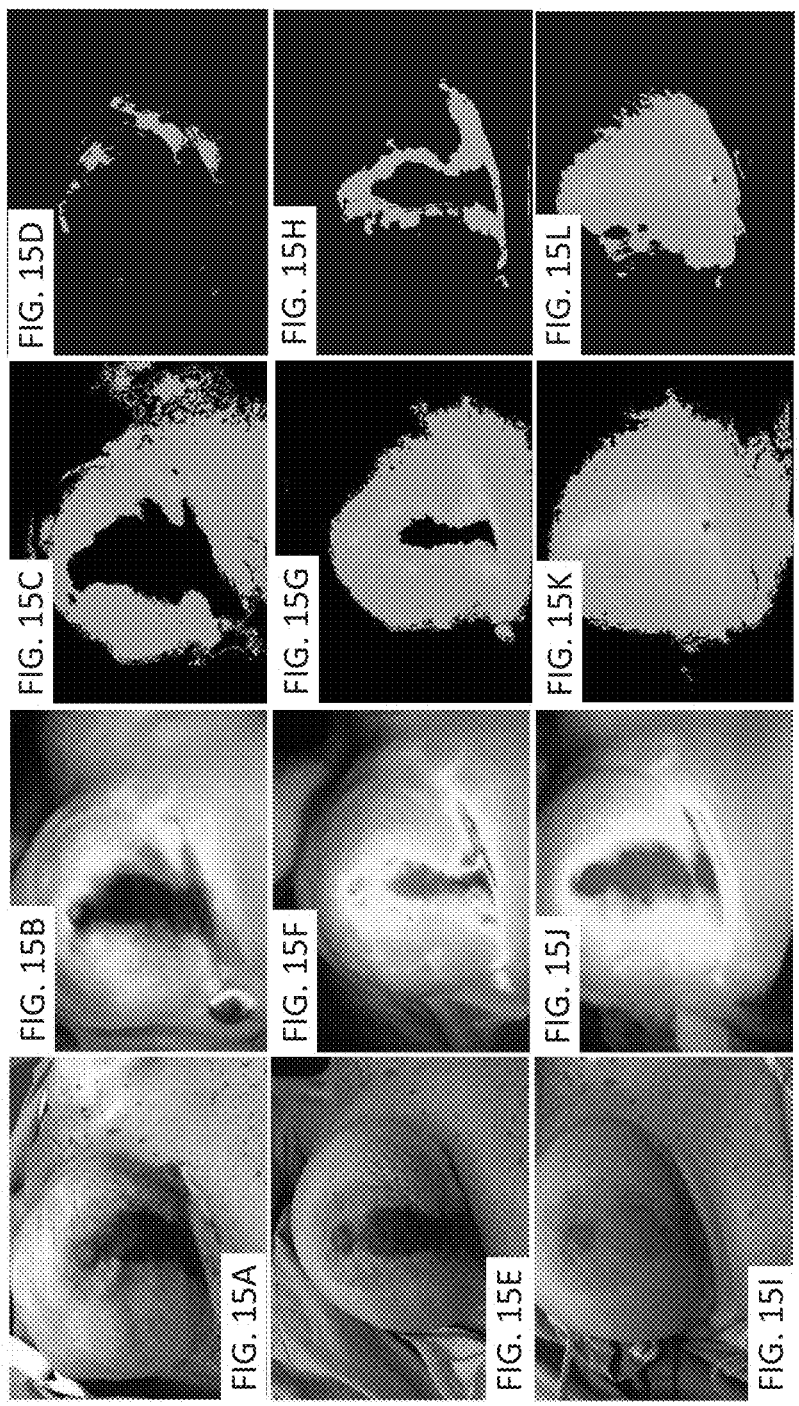

METHODS AND SYSTEMS FOR CHARACTERIZING TISSUE OF A SUBJECT

CROSS-REFERENCE TO RELATED APPLICATIONS

This application is a continuation of U.S. application Ser. No. 15/013,945 filed on Feb. 2, 2016, now U.S. Pat. No. 9,892,513, entitled "METHODS AND SYSTEMS FOR CHARACTERIZING TISSUE OF A SUBJECT" which claims priority to U.S. Provisional Application Ser. No. 62/110,609 filed on Feb. 2, 2015, entitled "METHODS AND SYSTEMS FOR PROCESSING A TIME SERIES OF ANGIOGRAPHY IMAGES OF TISSUE OF A SUBJECT" and U.S. Provisional Application Ser. No. 62/174,225 filed on Jun. 11, 2015, entitled "METHODS AND SYSTEMS FOR QUANTITATIVELY ASSESSING A WOUND IN TISSUE OF A SUBJECT", each of which is hereby incorporated by reference in its entirety.

FIELD

The present invention relates generally to the field of imaging, and more particularly to the processing of medical images for characterizing tissue of a subject.

BACKGROUND OF THE INVENTION

Blood flow is a generic term used to define movement of blood through blood vessels, which can be quantified in terms such as volumetric flow rate (i.e., volume/time) or travel speed (i.e., distance/time). Tissue perfusion is distinguished from vascular blood flow in that tissue perfusion defines movement of blood through blood vessels within a tissue volume. Tissue blood perfusion is often quantified in terms of volume/time/tissue volume, though on occasion tissue mass is used instead of tissue volume. More specifically, tissue perfusion relates to the microcirculatory flow of blood per unit tissue volume in which oxygen and nutrients are provided to, and waste is removed from, the capillary bed of the tissue being perfused. Perfusion is associated with nutritive blood vessels (i.e., micro-vessels known as capillaries) that comprise the vessels associated with exchange of metabolites between blood and tissue, rather than larger diameter non-nutritive vessels. However, compared to blood movement through the larger diameter blood vessels, blood movement through individual capillaries can be highly erratic, principally due to vasomotion, wherein spontaneous oscillation in blood vessel tone manifests as pulsation in erythrocyte movement. In certain cases, for example, vasomotion can result in a temporary arrest of blood flow within the capillary bed for periods of up to 20 seconds, in order to facilitate oxygen diffusion from the individual erythrocytes through the capillary vessel wall and into adjacent tissue being perfused. Consequently, spontaneous oscillations in capillary blood flow can be independent of heart beat, innervation, or respiration. Such flow cannot be defined simply in terms of volume/time; instead, it must be characterized on the basis of the aggregate amount of blood in all the blood vessel (i.e., capillary) segments within a given volume of tissue. This characterization is reflected in the fact that all the measurements of capillary blood movement include a tissue volume-related dimension.

There are many circumstances in which medical practitioners and other clinicians desire to correctly assess blood flow and/or tissue perfusion in tissue. For example, in treating patients with wounded tissue, clinicians must correctly assess blood flow and/or tissue perfusion in and around a wound site, since poor tissue perfusion will have an adverse effect on the healing process. An accurate assessment of blood flow and/or tissue perfusion increases the chances of successful healing of both acute (e.g., surgical) and chronic wounds. The assessment of perfusion dynamics is also important in other clinical applications, such as pre-surgical evaluation of patients undergoing plastic reconstruction procedures (e.g., skin flap transfers), or assessment of viability and function of cardiac tissue during cardiac surgery (e.g., coronary artery bypass graft surgery, a partial left ventriculectomy or a left ventricular reduction via the Batista surgical procedure, etc.).

Presently, clinicians may rely on clinical judgment based on subjective visual assessment and crude mechanical tests to assess tissue perfusion. One such crude mechanical test is a capillary refill test, in which the clinician applies pressure to an external capillary bed (e.g., by pressing on a nail bed) to cause blanching as blood is forced from the tissue, then measures the time needed for color to return after the pressure is released. However, such clinical judgment is subjective and not very precise.

Certain advanced practices have begun to use imaging technologies such as fluorescence imaging technologies for assessing blood flow and/or tissue perfusion. Fluorescence imaging technologies typically employ the administration of a bolus of an imaging agent (such as for example, indocyanine green (ICG), which binds with blood proteins in a subject) that subsequently circulates throughout the subject's vasculature and emits a fluorescence signal when illuminated with the appropriate excitation light. Fluorescence imaging systems acquire images of the emitted imaging agent fluorescence as the imaging agent bolus traverses the subject's tissue in the imaging field of view. The images are typically acquired as the bolus enters the tissue through arterial vessels, travels through the tissue's microvasculature, and exits the tissue through the venous vessels. When the images are displayed as video on a monitor, clinicians may observe this imaging agent transit in the vasculature represented as variations in fluorescence intensity with time. Based on their visual perception of the fluorescence intensity, clinicians may make a relative, qualitative determination regarding the blood flow and/or perfusion status of the tissue and its subsequent healing potential. However, a qualitative visual evaluation of such images is not always sufficient for a number of reasons, particularly in instances where the visual information is ambiguous. For instance, such visual evaluation is limited since many parameters, such as image brightness, image contrast and image noise, can be affected by factors other than the blood flow and/or perfusion properties of the tissue. Moreover, mere visual evaluation is subjective (e.g., visual evaluation may vary from clinician to clinician, one clinician's visual evaluation protocol may vary somewhat from patient to patient and/or from imaging session to imaging session) and does not support a standardized protocol for assessing blood flow and/or tissue perfusion. Finally, due to a clinician's lack of memory or inaccurate recollection of previous visual assessments, it can be challenging to reliably and consistently compare and track blood flow and/or perfusion status of a patient over time across multiple imaging sessions.

Thus, it is desirable to have methods and systems to process and/or present medical image data to the clinician in a manner that characterizes blood flow and/or tissue perfusion in an accurate, convenient, and easily understood fashion.

BRIEF SUMMARY OF THE INVENTION

Described here are variations of systems and methods for characterizing tissue of a subject. Generally, in one variation a system for characterizing tissue of a subject includes one or more processors, and memory having instructions stored thereon. In some variations, the instructions, when executed by the one or more processors, cause the system to receive a time series of fluorescence images of the tissue of the subject, wherein the images define a plurality of calculation regions; generate a plurality of time-intensity curves for the plurality of calculation regions; create a set of parameter values for each calculation region, wherein the parameter values approximate at least a portion of the time-intensity curve; generate a total rank value for each calculation region by comparing the sets of parameter values for the plurality of calculation regions; and convert the total rank values for the calculation regions into a ranking map image. The system may include a display, wherein the instructions cause the system to display the ranking map image on the display and/or cause the system to superimpose the ranking map image on an anatomical image of the tissue. The system may include a light source that provides an excitation light to induce fluorescence emission from a fluorescence imaging agent in the tissue. The system may include an image acquisition assembly that generates the time series of fluorescence images based on the fluorescence emission, such as, for example, a time series of fluorescence angiography images based on the fluorescence emission.

Generally, in another variation a system for characterizing tissue of a subject includes a reception unit arranged for receiving a time series of fluorescence images of the tissue of the subject, wherein the images define a plurality of calculation regions; a first generation unit arranged for generating for each of the plurality of calculation regions an individual time-intensity curve; a creation unit arranged for creating a set of parameter values for each calculation region, wherein the parameter values approximate at least a portion of the respective time-intensity curve; a second generation unit arranged for generating a total rank value for each of the calculation regions on the basis of the set of parameter values for that respective calculation region, and a conversion unit arranged for converting the total rank values for the calculation regions into a ranking map image.

In some variations of the system, the at least calculation region may be defined by one pixel or one voxel. In some variations, at least one of the parameter values is related to time properties of the time-intensity curve. In some variations, at least one of the parameter values is related to magnitude of intensity changes in the time-intensity curve. In some variations, at least one of the parameter values is a coefficient relating to a polynomial characterization of the time-intensity curve. In some variations, each parameter value is for a parameter type, and when the system compares the sets of parameter values, the system generates a set of numeric ranks for the parameter types for each calculation region. In some variations, when the system generates a total rank value for each calculation region, the system may sum the set of numeric ranks for each calculation region or may map a set of numeric metrics for each calculation region with a hash function. In some variations, when the system converts the total rank values into a ranking map image, the system correlates each total rank value to an intensity value.

Generally in one variation of a method for characterizing tissue of a subject, the method may include receiving a time series of fluorescence images of the tissue of the subject, wherein the images define a plurality of calculation regions; generating a plurality of time-intensity curves for the plurality of calculation regions; creating a set of parameter values for each calculation region, wherein the parameter values approximate at least a portion of the time-intensity curve; generating a total rank value for each calculation region by comparing the sets of parameter values for the plurality of calculation regions; and converting the total rank values for the calculation regions into a ranking map image. The method may be performed for use in medical imaging. The method may be performed at a computer system including one or more processors and memory.

Generally in another variation of a method, a computer-implemented method for visualization of angiography image information comprises: retrieving a time series of angiography images of tissue of a subject; defining a plurality of calculation regions, each calculation region relating to a corresponding image position in each of the angiography images of the time series; for each calculation region, generating a time-intensity curve for that calculation region in the time series of angiography images; for each calculation region, calculating a rank value for that calculation region based on one or more of parameters derived from the time-intensity curve; and generating a viewable image in which on the image position of each calculation region, an indication is provided of the calculated rank value for that calculation region. In some variations, the time series of angiography images may relate to a single image series obtaining event.

In some variations of the method, the at least one calculation region is defined by one pixel or one voxel. In some variations, at least one of the parameter values is related to time properties of the time-intensity curve. For example, the parameter value may be for (or comprise) one of the following parameter types: (i) duration of a region of increasing intensity of the time-intensity curve, (ii) duration of a region of high intensity of the time-intensity curve, (iii) duration of a region of a plateau of the time-intensity curve, (iv) duration of a region of decreasing intensity of the time-intensity curve, or a combination thereof. As another example, the parameter value may be for (or comprise) one of the following parameter types: (i) duration of a perfusion onset phase of the time-intensity curve, (ii) duration of an arterial phase of the time-intensity curve, (iii) duration of a micro-vascular phase of the time-intensity curve, (iv) duration of a venous phase of the time-intensity curve, or a combination thereof. As another example, the parameter value may be for (or comprise) one of the following parameter types: (i) the time to the onset of increasing fluorescence intensity, (ii) the time for rapid or most rapid fluorescence intensity increase, (iii) the time for rapid or most rapid fluorescence intensity decrease, (iv) rate of change in fluorescence intensity for any of the above-described regions of the time-intensity curve, or a combination thereof.

In some variations, at least one of the parameter values is related to magnitude of intensity changes in the time-intensity curve. For example, the parameter value may be for (or comprise) one of the following parameter types: (i) intensity change within a region of increasing intensity of the time-intensity curve, (ii) intensity change within a region of high intensity of the time-intensity curve, (iii) intensity change within a region of decreasing intensity of the time-intensity curve, or a combination thereof. As another example, the parameter value may be for (or comprise) one of the following parameter types: (i) intensity change during a perfusion onset phase of the time-intensity curve, (ii) intensity change during an arterial phase of the time-intensity curve, (iii) intensity change during a micro-vascular phase of the time-intensity curve, (iv) intensity change during a venous phase of the time-intensity curve, or a combination thereof. As another example, the parameter value may be for (or comprise) one of the following parameter types: (i) intensity change during a period of rapid or most rapid fluorescence intensity increase, (ii) intensity change during a period of rapid or most rapid fluorescence intensity decrease, or a combination thereof.

In some variations, at least one of the parameter values is a coefficient value relating to a polynomial characterization of the time-intensity curve. In some variations, each parameter value may be a value for a parameter type and comparing the sets of parameter values comprises generating a set of numeric ranks for the parameter types for each calculation region.

In some variations, generating a total rank value for each calculation region includes summing the set of numeric ranks for each calculation region. In some variations, generating a total rank value for each calculation region includes mapping a set of numeric metrics for each calculation region with a hash function. The hash function may include, for example, a cyclic redundancy check, a pairing function, etc. In some variations, converting the total rank values into a ranking map comprises correlating each total rank value to an intensity value, and/or correlating each total rank value to a grayscale or color display value. In some variations, the method comprises displaying the ranking map image on a display. The ranking map image may be superimposed on an anatomical image of the tissue of the subject. In some variations, the method includes generating the time series of fluorescence images using a fluorescence imaging system that captures transit of a bolus of a fluorescence imaging agent moving through the tissue. For example, the fluorescence imaging agent may comprise indocyanine green, fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof. In some variations, the time series of fluorescence images includes a time series of fluorescence angiography images.

Generally, in one variation of a system for characterizing a wound in a target tissue region of a subject, the system includes: one or more processors; and memory having instructions stored thereon. The instructions, when executed by the one or more processors, may cause the system to: receive a time series of fluorescence images of the target tissue region of the subject, wherein the images define a plurality of calculation regions; generate a plurality of time-intensity curves for the plurality of calculation regions; create one or more parameter values for each calculation region, wherein the one or more parameter values approximates at least a portion of the time-intensity curve; generate a total rank value for each calculation region by comparing the sets of parameter values for the plurality of calculation regions; generate a data set comprising modified total rank values, wherein the modified total rank values are based at least in part on a comparison between the total rank values and a reference value; and generate a wound index value based on at least a portion of the data set corresponding to calculation regions located in the wound. In some variations, the system includes a display, wherein the instructions cause the system to display the ranking map image on the display. In some variations, the system includes a light source that provides an excitation light to induce fluorescence emission from a fluorescence imaging agent in the tissue. In some variations, the system includes an image acquisition assembly that generates the time series of fluorescence images based on the fluorescence emission. In some variations, the time series of fluorescence images includes a time series of fluorescence angiography images based on the fluorescence emission.

Generally, in another variation of a system for characterizing a wound in a target tissue region of a subject, the system includes a reception unit arranged for receiving a time series of fluorescence images of the target tissue region of the subject, wherein the images define a plurality of calculation regions; a first generation unit arranged for generating for each of the plurality of calculation regions an individual time-intensity curve; a creation unit arranged for creating a set of parameter values for each calculation region, wherein the parameter values approximate at least a portion of the respective time-intensity curve; a second generation unit arranged for generating a total rank value for each of the calculation regions on the basis of the set of parameter values for that respective calculation region; a third generation unit arranged for generating a data set comprising modified total rank values, wherein the modified total rank values are based at least in part on a comparison between the total rank values and a reference value; and a fourth generation unit arranged for generating a wound index value based on at least a portion of the data set corresponding to calculation regions located in the wound.

In some variations of the system, at least one calculation region is defined by one pixel or one voxel. In some variations, when the system generates a data set, the system modulates at least a portion of the total rank values. In some variations, the system modulates a first portion of the total rank values with a first modulation function to generate a first modulated data set, and modulates a second portion of the total rank values with a second modulation function to generate a second modulated data set. In some variations, the first modulation function is an identity function. In some variations, the second modulation function causes the second modulated data set to equal zero. In some variations, the first modulated data set includes a plurality of wound characterization values, and the second modulated data set comprises a plurality of non-wound characterization values. In some variations, the modified total rank values are based on a comparison of the first and second modulated data set to the reference value. In some variations, the reference value includes a reference rank value, wherein the reference rank value is based on a reference time-intensity curve for a time series of reference fluorescence images, and wherein the time series of reference fluorescence images is of reference tissue.

In some variations, the wound index value is an average of at least a portion of the data set corresponding to calculation regions located in the wound. In some variations, the wound index value is generated by summing the modified total rank values corresponding to calculation regions located in the wound and dividing the sum by the number of pixels or voxels in the fluorescence images. In some variations, the wound index value is generated by summing the modified total rank values corresponding to calculation regions located in the wound and dividing the sum by the number of pixels or voxels in the calculation regions corresponding to calculation regions located in the target tissue region.

Generally, a method for characterizing a wound in a target tissue region of a subject includes receiving a time series of fluorescence images of the target tissue region of the subject, wherein the images define a plurality of calculation regions; generating a plurality of time-intensity curves for the plurality of calculation regions; creating one or more parameter values for each calculation region, wherein the one or more parameter values approximates at least a portion of the time-intensity curve; generating a total rank value for each calculation region by comparing the sets of parameter values for the plurality of calculation regions; generating a data set comprising modified total rank values, wherein the modified total rank values are based at least in part on a comparison between the total rank values and a reference value; and generating a wound index value based on at least a portion of the data set corresponding to calculation regions located in the wound. The method may be performed for use in medical imaging. The method may be performed at a computer system including one or more processors and memory.

In some variations of the method, at least one calculation region is defined by one pixel or one voxel. In some variations, generating a data set includes modulating at least a portion of the total rank values. In some variations, modulating at least a portion of the total rank values comprises modulating a first portion of the total rank values with a first modulation function to generate a first modulated data set, and modulating a second portion of the total rank values with a second modulation function to generate a second modulated data set. In some variations, the first and second modulation functions are different. In some variations, the first modulation function is an identity function. In some variations, the second modulation function causes the second modulated data set to equal zero. In some variations, the first modulated data set includes a plurality of wound characterization values, and the second modulated data set includes a plurality of non-wound characterization values.

In some variations, generating a data set includes comparing the first and second modulated data sets to the reference value. In some variations, the reference value may include a reference rank value, wherein the reference rank value is based on a reference time-intensity curve for a time series of reference fluorescence images. In some variations, the time series of reference fluorescence images is of reference tissue. In some variations, the reference tissue may be healthy tissue in the subject, healthy tissue in the target tissue region of the subject, or tissue of one or more healthy third-party subjects. In some variations, the reference value is at least partially based on a background metric of the time series of fluorescence images. In some variations, the reference value is modified by a tolerance value, a multiplier, or an average of multiple reference values.

In some variations, generating a wound index value includes averaging at least a portion of the data set corresponding to calculation regions located in the wound. In some of these averaging at least a portion of the data set includes summing the modified total rank values corresponding to calculation regions located in the wound and dividing the sum by the number of pixels or voxels in the fluorescence images. In some of these variations, averaging at least a portion of the data set includes summing the modified total rank values corresponding to calculation regions located in the wound and dividing the sum by the number of pixels or voxels in the calculation regions corresponding to calculation regions located in the target tissue region.

In some variations, the method includes displaying the wound index value on a display. In some variations, the method includes converting the total rank values for the calculation regions into a ranking map image, and displaying the ranking map image with the wound index value on the display. In some variations, the method includes generating the time series of fluorescence images using a fluorescence imaging system that captures transit of a bolus of a fluorescence imaging agent moving through the tissue. For example, the fluorescence imaging agent may comprise indocyanine green, fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof. In some variations, the time series of fluorescence images includes a time series of fluorescence angiography images. In some variations, the time series of fluorescence images includes a time series of fluorescence angiography images.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A schematically illustrates a normal wound healing process. FIG. 5B schematically illustrates a chronic wound healing process.

FIG. 6 is an illustrative depiction of an exemplary fluorescence imaging system configured to characterize tissue of a subject.

FIG. 7 is an illustrative depiction of an exemplary illumination module of a fluorescence imaging system configured to characterize tissue of a subject.

FIG. 8 is an exemplary camera module of a fluorescence imaging system configured to characterize tissue of a subject.

FIGS. 9A-9F depict exemplary images relating to an application of the methods and systems to wound care.

FIGS. 12-12H depict exemplary images relating to an application of the methods and systems to wound management of a traumatic fracture wound.

FIGS. 15A-15L depict exemplary images relating to an application of the methods and systems to breast reconstructive surgery.

DETAILED DESCRIPTION OF THE INVENTION

Reference will now be made in detail to implementations and embodiments of various aspects and variations of the invention, examples of which are illustrated in the accompanying drawings.

Methods for Characterizing Tissue of a Subject

Figure 1:
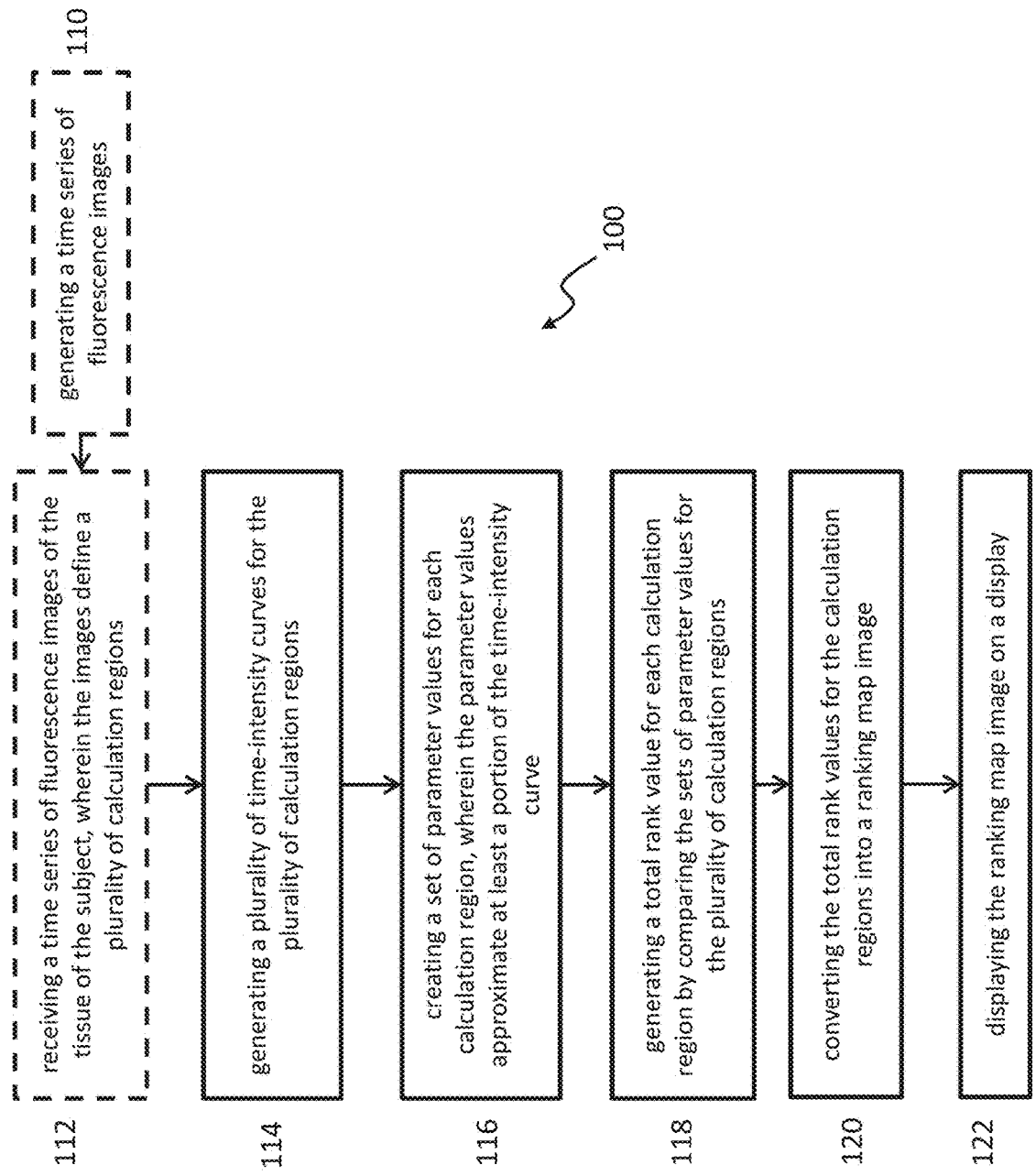
FIG. 1 is an illustrative block diagram of an exemplary method for characterizing tissue of a subject.

As shown in FIG. 1, an example of a method 100 for characterizing tissue of a subject may include: receiving a time series of fluorescence images of the tissue of the subject 112, wherein the images define a plurality of calculation regions, generating a plurality of time-intensity curves for the plurality of calculation regions 114, creating a set of parameter values for each calculation region 116, wherein the parameter values approximate at least a portion of the time-intensity curve, generating a total rank value for each calculation region by comparing the sets of parameter values for the plurality of calculation regions 118, and converting the total rank values for the calculation region into a ranking map image 120. In some variations, the method may further include generating the time series of fluorescence images 110, and/or displaying the ranking map image on a display 122.

In some variations, at least a portion of the method may be performed by a computer system located separate from a medical imaging system. For instance, some or all of the steps of receiving a time series of fluorescence images 112, generating a plurality of time-intensity curves 114, creating a set of parameter values 116, generating a total rank value for each calculation region 118, and converting the total rank values into a ranking map image 120 may be performed by a computer system at an off-site location that is remote from a clinical site (e.g., where a fluorescence imaging system is situated) or by a computer system that is located at a clinical setting but not embodied in an imaging system. In these variations, the time series of fluorescence images may be received as a result of a transfer of image data from a data storage medium (e.g., hard drive, cloud storage, etc.) or through a network communication (e.g., wired connection, Internet, wireless network based on a suitable wireless technology standard, etc.). For instance, the method may involve a client-server architecture, such that an imaging system may include client hardware that sends image data to a computing server and loads processed data (e.g., ranking map image or interim outputs of various steps of the methods described herein) back onto the imaging system. After the client hardware in the imaging system loads the processed data, the imaging system may further process the data and/or display the processed data in accordance with the methods described herein.

In some variations, at least a portion of the method is performed by one or more processors at a computer system incorporated into a medical imaging system, such as at a clinical site. For example, some or all of the steps of receiving a time series of fluorescence images 112, generating a plurality of time-intensity curves 114, creating a set of parameter values 116, generating a total rank value for each calculation region 118, and converting the total rank values into a ranking map image 120 may be performed by a computer system in a medical imaging system. In some of these variations, the method may further include generating the time series of fluorescence images 110 prior to receiving the time series of fluorescence images.

As described above, current medical imaging technologies such as fluorescence imaging systems provide limited opportunity for clinicians to accurately assess blood flow and/or tissue perfusion in tissue of a subject. For instance, when visually evaluating fluorescence images that capture transit of a dye bolus through tissue, clinicians' assessment of blood flow and/or tissue perfusion is confounded by parameters (e.g., brightness, image contrast, image noise) that are independent of perfusion properties of the tissue. Additionally, clinicians' mere visual evaluation of the images is subjective and may vary from clinician to clinician, patient to patient, and/or imaging session to imaging session. Furthermore, due to a clinician's lack of memory or inaccurate recollection of previous visual assessments, there is no way to reliably and consistently compare and track blood flow and/or perfusion status of a patient over time across multiple imaging sessions.

The methods and systems described herein for characterizing tissue process and present image data to the user in a manner that enables more effective clinical decision making. In particular, the ranking map image may be a spatial map that concisely shows relative differences between image elements such as, for example, pixels (or voxels), or relative differences between different regions of imaged tissue, with respect to clinically-relevant parameters. In some variations, the ranking map image may be a visualization of how different areas of the imaged tissue vary in healing status, tissue property, and/or other tissue condition. For example, the ranking map image may visualize inflammation, malignancy, disease, or other abnormality of the tissue in a way that is easily perceptible and identifiable by a human being. As described further herein, these quantified visualizations reduce ambiguity and the effect of clinicians' subjectivity, by facilitating a standardized protocol for assessing blood flow and/or tissue perfusion and providing a way to compare and track assessments of a patient over time across multiple imaging sessions. Thus, these quantified visualizations enable a clinician to make more consistent clinical assessments and/or medical treatment decisions.

Although various exemplary embodiments are described in the specification in the context of a time series of fluorescence images, the method may be applied to other sources of images generated as a time series which relate to a dynamic behavior of an imaging agent in the tissue and for other clinical purposes. For example, the images may be derived from computerized tomographic (CT) angiography with a radio-opaque contrast dye for blood flow and tissue perfusion assessment. As another example, the images may be derived from positron emission tomography (PET) using a fluorodeoxyglucose (FDG) or other radiotracer to evaluate metabolic activity and potentially assess pathology and/or provide information usable for assessing pathology. As another example, the images may be derived from contrast-enhanced ultrasound imaging employing the use of gas-filled microbubble contrast medium administered intravenously to the systemic circulation. Such ultrasonic imaging using microbubble contrast agents enhances the ultrasound backscatter or reflection of the ultrasound waves to produce a unique sonogram with increased contrast due to the high echogenicity (i.e., ability of an object to reflect the ultrasound waves) difference between the gas in the microbubbles and the soft tissue. Contrast-enhanced ultrasound can be used, for example, to image blood perfusion and blood flow in organs.

Generating the Time Series of Images

In some variations, as shown in FIG. 1, the method includes generating a time series of fluorescence images 110. The time series of fluorescence images of the tissue of the subject may be generated by fluorescence imaging technologies employing a fluorescence imaging agent such as, for example, indocyanine green (ICG) dye as a fluorescence imaging agent. ICG, when administered to the subject, binds with blood proteins and circulates with the blood in the tissue. Although reference is made in the specification to a fluorescence agent or a fluorescence dye, other suitable imaging agents may be used depending on the type of imaging technology being employed to generate the time series of images.

In some variations, the fluorescence imaging agent (e.g., ICG) may be administered to the subject as a bolus injection, in a suitable concentration for imaging. In some variations where the method is performed to assess tissue perfusion, the fluorescence imaging agent may be administered to the subject by injection into a vein or artery of the subject such that the dye bolus circulates in the vasculature and traverses the microvasculature. In some variations in which multiple fluorescence imaging agents are used, such agents may be administered simultaneously (e.g., in a single bolus), or sequentially (e.g., in separate boluses). In some variations, the fluorescence imaging agent may be administered by a catheter. In some variations, the fluorescence imaging agent may be administered to the subject less than an hour in advance of performing the measurements for generating the time series of fluorescence images. For example, the fluorescence imaging agent may be administered to the subject less than 30 minutes in advance of the measurements. In other variations, the fluorescence imaging agent may be administered at least 30 seconds in advance of performing the measurements. In some variations, the fluorescence imaging agent may be administered contemporaneously with performing the measurements.

In some variations, the fluorescence imaging agent may be administered in various concentrations to achieve a desired circulating concentration in the blood. For example, in some variations for tissue perfusion assessment where the fluorescence imaging agent is ICG, the fluorescence imaging agent may be administered at a concentration of about 2.5 mg/mL to achieve a circulating concentration of about 5 μM to about 10 μM in blood. In some variations, the upper concentration limit for the administration of the fluorescence imaging agent is the concentration at which the fluorescence imaging agent becomes clinically toxic in circulating blood, and the lower concentration limit is the limit for instruments used to acquire the time series of fluorescence images that detect the fluorescence imaging agent circulating in blood. In some variations, the upper concentration limit for the administration of the fluorescence imaging agent is the concentration at which the fluorescence imaging agent becomes self-quenching. For example, the circulating concentration of ICG may range from about 2 μM to about 10 mM.

Thus, in one aspect, the method may comprise administration of a fluorescence imaging agent or other imaging agent to the subject, and generation or acquisition of the time series of fluorescence images prior to processing the image data. In another aspect, the method may exclude any step of administering the fluorescence imaging agent or other imaging agent to the subject. For instance, the time series of fluorescence images may be based on measurements of a fluorescence imaging agent such as, for example, indocyanine green (ICG) dye that is already present in the subject and/or based on autofluorescence response (e.g., native tissue autofluorescence or induced tissue autofluorescence), or measurements of a combination of autofluorescence and exogenous fluorescence arising from a fluorescence imaging agent.

In some variations, a suitable fluorescence imaging agent is an agent which can circulate with the blood (e.g., a fluorescence dye which can circulate with a component of the blood such as lipoproteins or serum plasma in the blood) and which fluoresces when exposed to appropriate excitation light energy. The fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic Acid (5-ALA), or a combination thereof.

In some variations, the fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Any diluent or carrier which will maintain the fluorescence imaging agent in solution may be used. As an example, ICG may be reconstituted with water. In some variations, once the fluorescence imaging agent is reconstituted, it may be mixed with additional diluents and carriers. In some variations, the fluorescence imaging agent may be conjugated to another molecule, (e.g., a protein, a peptide, an amino acid, a synthetic polymer, or a sugar) so as to enhance solubility, stability, imaging properties or a combination thereof. Additional buffering agents may optionally be added including Tris, HCl, NaOH, phosphate buffer, HEPES.

In some variations, the time series of fluorescence images comprises a plurality of individual image frames (e.g., fluorescence image frames), or data representative of individual frames, ordered consecutively by acquisition time. For example, a time series of fluorescence images can be acquired using an ICG-based fluorescence imaging system, where the subject receives an intravenous injection of ICG immediately prior to procedure, and the tissue is illuminated with light at ICG's excitation wavelengths while the resulting fluorescence emission from the dye as it transits the target tissue is imaged. The fluorescence images may subsequently also stored as a series of individual frames, or data representative of individual frames (e.g., compressed video), ordered consecutively by their acquisition time.

In some variations, the individual image frames of the time series are spatially aligned or registered. For example, a typical time series of fluorescence images may be recorded over 2 to 3 minutes, during which some subjects' movements may be unavoidable. As a result, the same anatomical features can appear at different positions in image frames acquired at different times during the image time series acquisition period. Since such misalignments can introduce errors in the subsequent analysis where the level of fluorescence for each pixel or a group of pixels is followed over time. To help reduce errors, the generated image frames may be spatially aligned (registered) with each other. In some variations, image registration or alignment refers to a process of determining the spatial transform that maps points from one image to homologous points in the second image.

Image registration may be an iterative process. For example, according to an exemplary embodiment, image registration may use one or more of the following set of components: two input images, a transform, a metric, an interpolator, and an optimizer. A transform maps the fixed image space into the moving image space. An optimizer is required to explore the parameter space Insight Segmentation and Registration Toolkit (ITK) (itk.org/) based implementation of the transform in search of optimal values of the metric may be used. The metric compares how well the two images match each other. Finally, the interpolator evaluates the intensities of the moving image at non-grid positions. To align the entire time series of fluorescence images, this procedure is executed for all the frames included in the analysis. The component loops through the range of input series frames, subtracts a background image for baseline correction and applies noise-reduction filters, then registers consecutive pairs of images.

In some variations, the time series of fluorescence images is pre-processed to, for example, extract selected data, calculate a baseline intensity, perform an image quality improvement process, or a combination thereof.

Extraction of selected data may, for example, comprise cropping to locate and exclude certain data from the image time series data. For example, during a fluorescence imaging procedure of the subject, an operator might start recording the time series of fluorescence images well before the fluorescence imaging agent reaches the target tissue As a result, the time series of fluorescence images might have a significant number of "dark" frames in the beginning, thus adding unnecessary computational time for the frames that contain no meaningful data. To mitigate the problem, cropping can be used to remove those "dark" frames from the beginning of the time series of fluorescence images. In addition, when the subject is injected with the fluorescence imaging agent (e.g., ICG), the fluorescence signal from the imaging agent as it transits the target tissue typically proceeds through a series of phases: rapid increase of fluorescence intensity as the imaging agent enters the tissue through arterial vessels, followed by a period of stable fluorescence as the imaging agent traverses the microvasculature, then slow decrease in fluorescence intensity due to the venous outflow of the imaging agent, followed by a period of residual fluorescence as any imaging agent retained in the lining of the vasculature released into the bloodstream. This last "residual" phase can last for several minutes and, as it is not directly indicative of blood flow, does not typically provide meaningful perfusion information. Thus, cropping may be used to locate and exclude the residual phase from subsequent steps of analysis.

In some variations, pre-processing may include calculation of the baseline intensity. For example, when the time series of fluorescence images is being generated by a fluorescence imaging system, various external factors can contribute to the fluorescence of the recorded series, such as camera noise, thermal noise, and/or presence of residual fluorescence dye from an earlier injection. In order to minimize the influence of such factors on the analysis, the baseline intensity may be calculated for every series, and the analysis of the data may be adjusted accordingly.

In some variations, pre-processing may include an image quality validation process. Such a process may comprise a starting brightness test in embodiments where, for example, the acquisition of the time series of fluorescence images has started too late and the imaging agent has already begun its transit of the target tissue by the time the first frame was captured. In this scenario, the time series of fluorescence images cannot be reliably analyzed or processed since the information relating to the start of perfusion has been lost. As a result, such series data would be rejected.

In some variations, the image quality validation process may comprise a brightness change test. Such a test may be used, for example, in instances where the fluorescence imaging system was suddenly moved during the image acquisition, foreign objects appeared in the field of view, or a light from an external source illuminated the scene while the series was being captured. All of these events may significantly distort the results of any subsequent analysis. Accordingly, the time series of fluorescence images subjected to such a test might fail the validation procedure (be identified as being unsuitable for further processing). According to an exemplary embodiment, the brightness change test comprises a calculation of the difference between average intensities of neighboring frames in the time series of fluorescence images and compares it to a selected intensity difference threshold. In order to pass validation, the differences in intensities of all consecutive frames must be within the limit specified by the selected intensity difference threshold.

In some variations, the image quality validation process may comprise an intensity peak location test to check that the acquisition of the time series of fluorescence images has not been stopped prematurely. For example, the intensity peak location test ensures that a sufficient number of frames have been acquired to cover all phases of the dye bolus transit through the tissue. According to an exemplary embodiment, the fluorescence intensity peak location test comprises finding the frame with the maximum average fluorescence intensity and verifying that it is not the last frame in the time series of fluorescence images. Should this condition fail, it will be a strong indication that the fluorescence intensity values have not reached their maximum yet and such a time series of fluorescence images is not suitable for further analysis.

In some variations, the image quality validation process may yet further comprise a maximum fluorescence intensity test. The purpose of the test is to filter out the time series of fluorescence images in which the images are too dark (majority of pixels fall below a pre-defined threshold) or over-saturated (majority of pixels are above a pre-defined saturation threshold).

The curvature of the tissue surface, excessive movement during the image acquisition procedure, dark or oversaturated images, foreign objects within imaged area and external light or shading can affect the quality of the time series of fluorescence images, and thus the subsequent processing of such image data. To mitigate these problems, a well-structured imaging protocol and a fluorescence imaging system designed to minimize such issues may be used.

The time series of images may define a plurality of calculation regions. Each calculation region may be an image element such as, for example, a single pixel or group of pixels, a voxel or group of voxels, or some other spatially defined area or volume in the time series of fluorescence images. Each calculation region may be identical in size to all other calculation regions, or may be different in size compared to some or all other calculation regions. In one variation, the boundaries and/or distribution of one or more calculation regions may be pre-defined (e.g., a calculation region for each pixel or voxel, or a calculation region for each 2×2 group of pixels or 2×2×2 block of voxels). In another variation, the boundaries and/or distribution of one or more calculation regions may be defined by a user such as the clinician.

Generating a Plurality of Time-intensity Curves

In some variations, as shown in FIG. 1, the method includes generating a plurality of time-intensity curves for the plurality of calculation regions 114. Each time-intensity curve corresponds to a respective calculation region in the fluorescence images. For each of some or all of the plurality of calculation regions 114, an individual time-intensity curve may be generated. As shown schematically in FIGS. 2A and 2B, a given time-intensity curve 212 (FIG. 2B) corresponding to a particular calculation region 210 (FIG. 2A) describes the intensity of fluorescence signal observed in that calculation region throughout the time series of fluorescence images. In some variations, a time-intensity curve describes all phases (e.g. arterial, micro-vascular, venous and residual in angiography applications), a subset of a phase or of a combination of phases, a subset of all phases, or a derivative thereof (including, for example, determinations based upon first and second time derivatives associated with changes in fluorescent intensity on a pixel-by-pixel, or voxel-by-voxel, basis). All or some of the time-intensity curves may be generated by a processor embodied in a fluorescence imaging system that generated the fluorescence images, or by a processor remote from the fluorescence imaging system that generated the fluorescence images.

Figure 2:
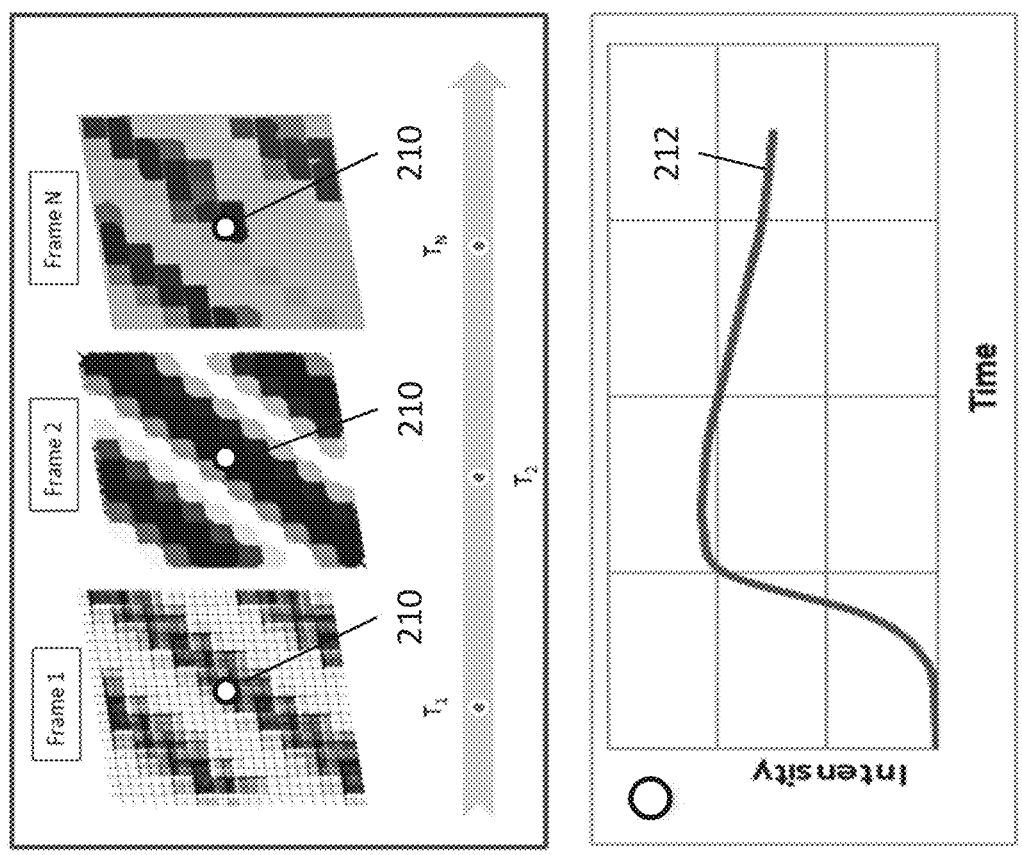
FIG. 2A is an illustrative depiction of a time series of images.
FIG. 2B is an illustrative depiction of a time-intensity curve generated for a calculation region in the time series of images.
Figure 3:
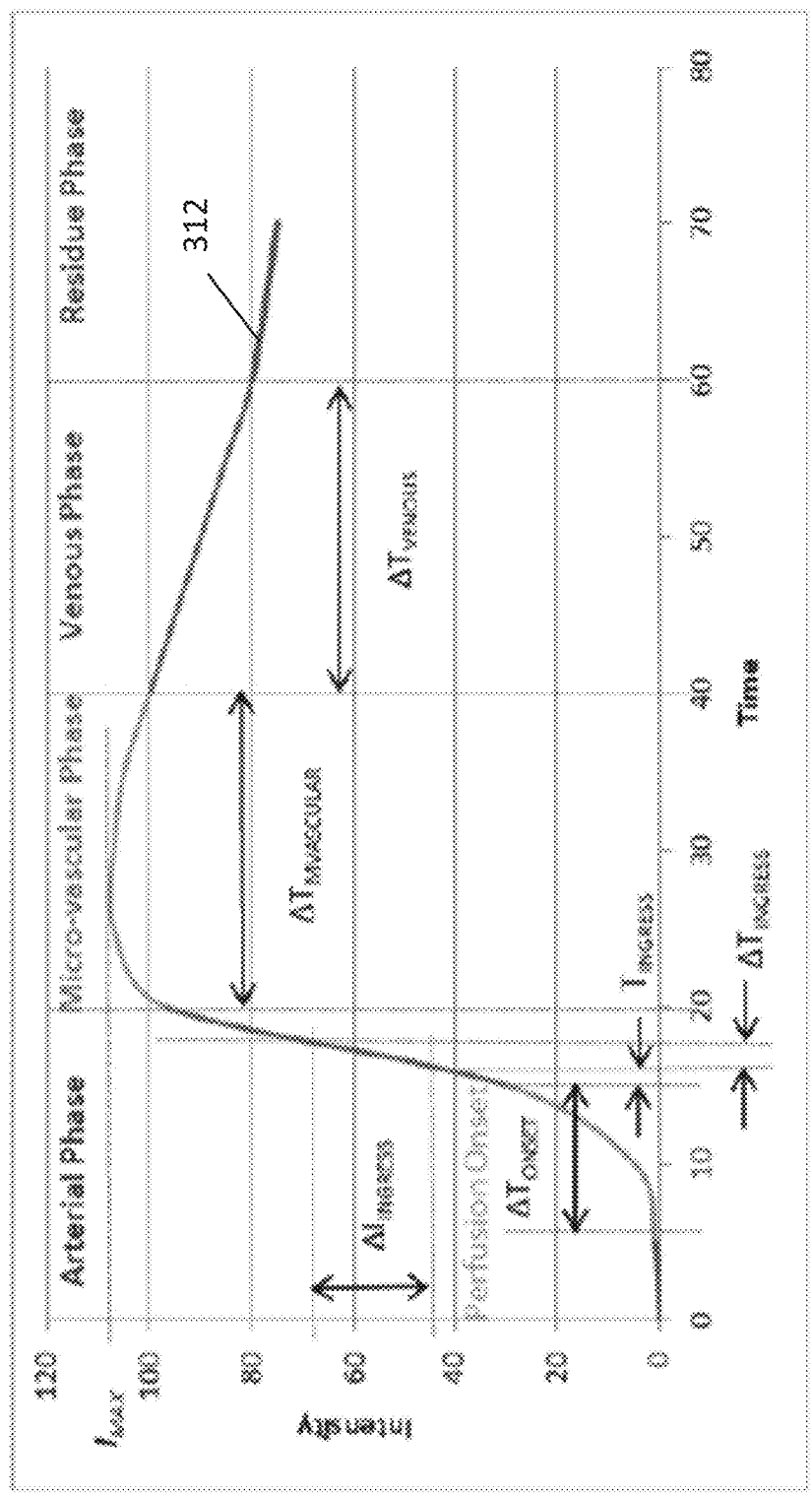
FIG. 3 is an exemplary time-intensity curve with a plurality of exemplary parameters that approximate or otherwise characterize the time-intensity curve.

In some variations, as shown in FIG. 2B, a time-intensity curve 212 comprises a region of increasing intensity, a region of peak intensity, a plateau region, a region of decreasing intensity, or a combination thereof. In the context of fluorescence imaging (e.g., fluorescence angiography), as shown in FIG. 3, a time-intensity curve 312 may represent the transit of a fluorescence imaging agent (e.g., a fluorescence dye) bolus through the tissue as a series of phases: an arterial phase, a micro-vascular phase, a venous phase, a residual phase, or a combination thereof.

The shape of the time-intensity curve (or a portion thereof), an area under the time-intensity curve, or a combination thereof may be indicative of distribution of the fluorescence imaging agent in the tissue of the subject, blood flow in the tissue, or a combination thereof. In some applications, the distribution of the imaging agent in the tissue of the subject represents a property of the tissue, a condition of the tissue (e.g., inflammation, malignancy, abnormality, disease) or a combination thereof.

Creating a Set of Parameter Values for Each Calculation Region

In some variations, as shown in FIG. 1, the method includes creating a set of parameter values for each calculation region 116, wherein the parameter values characterize or approximate at least a portion of the time-intensity curve. In some variations, one or more of the parameter types may be defined with respect to time properties of the curve. For example, one or more of the parameter types may be related to duration of a particular region of the time-intensity curve, such as: (i) the duration of a region of increasing intensity of the time-intensity curve, (ii) the duration of a region of peak or high intensity of the time-intensity curve, (iii) the duration of a region of a plateau of the time-intensity curve, or (iv) the duration of a region of decreasing intensity of the time-intensity curve. In the context of fluorescence imaging (e.g., fluorescence angiography), one or more of the parameter types may be related to the duration of a perfusion onset phase, an arterial phase, a micro-vascular phase, or venous phase. As another example, one or more of the parameter types may be related to a defined period of elapsed time, between one defined event (e.g. the beginning of the raw or pre-processed time series of fluorescence images) and a second defined event, such as: (v) the time to the onset of increasing fluorescence intensity. As another example, one or more of the parameter types may be related to a defined period of time with key rate-of-change or other intensity characteristics, such as: (vi) the time for rapid or most rapid fluorescence intensity increase, the time for rapid or most rapid fluorescence intensity decrease, and/or rate of change in fluorescence intensity for any of the above-described regions of the time-intensity curve.

In some variations, one or more of the parameter types may be defined with respect to fluorescence intensity changes over certain regions of the time-intensity curve. For example, one or more of the parameter types may relate to the intensity change over a particular region of the time-intensity curve, such as: (i) the intensity change within a region of increasing intensity of the time-intensity curve, (ii) the intensity change within a region of high or peak intensity of the time-intensity curve, or (iii) the intensity change within a region of decreasing intensity of the time-intensity curve. In the exemplary context of fluorescence imaging (e.g., fluorescence angiography), one or more of the parameter types may be related to the intensity change during a perfusion onset phase, an arterial phase, a micro-vascular phase, or a venous phase. As another example, one or more of the parameter types may be related to the intensity change over a defined period of elapsed time between one defined event (e.g., the beginning of the raw or pre-processed time series of fluorescence images) and a second defined event, such as (iv) the intensity change during the onset to increasing fluorescence intensity. As another example, one or more of the parameter types may be related to the intensity change over a defined period of time with key rate-of-change or other intensity characteristics, such as: (v) the intensity change during the period of rapid or most rapid fluorescence intensity increase, (vi) the intensity change during the period of high fluorescence intensity, and/or (vii) the intensity change during the period of rapid or most rapid fluorescence intensity decrease.

In some variations, one or more of the parameter types may be based on a numerical curve-fitting algorithm, which in certain embodiments, may increase the accuracy with which the time-intensity curve is represented. However, the parameter values for the calculation regions may include values for any suitable parameter types that approximate or otherwise characterize at least a portion of the time-intensity curve.

Generating a Total Rank Value for Each Calculation Region

In some variations, as shown in FIG. 1, the method comprises generating a total rank value for each calculation region 118 in the time series of images. Generating a total rank value for each calculation region results in a quantitative description of how the time-intensity curve for each calculation region compares to the time-intensity curves of other calculation regions. More specifically, the total rank value for each calculation region may reflect how the parameter values (which characterize or approximate at least a portion of the time-intensity curve) for that calculation region quantitatively compare to (or "rank" against) the parameter values for every other calculation region.

In a first variation of generating a total rank value 118, the total rank value for each calculation region may be based on a set of numeric ranks for that calculation region. In these variations, each numeric rank, or subrank, is based on how a particular parameter for that calculation region compares or ranks against that parameter for all other calculation regions. In other words, a numeric rank is generated or otherwise assigned for each parameter value for each calculation region, such that each calculation region is associated with a set of numeric ranks for the set of parameter values.

In the context of fluorescence imaging (e.g., fluorescence angiography), the time-intensity curve for each calculation region may, for example, be quantified by the following parameters which are illustrated in FIG. 3: the duration of the onset phase ($\Delta T_{ONSET}$), the fluorescence intensity change within a fixed time interval during the arterial phase ($\Delta I_{INGRESS}$), the duration of the micro-vascular phase ($\Delta T_{MVASCULAR}$), and the duration of the venous phase ($\Delta T_{VENOUS}$). With respect to one calculation region, a first numeric rank that corresponds to $\Delta T_{ONSET}$ is generated based on how $\Delta T_{ONSET}$ for that calculation region ranks relative to (is longer or shorter than) $\Delta T_{ONSET}$ for all other calculation regions. A second numeric rank that corresponds to $\Delta I_{INGRESS}$ is generated based on how $\Delta_{INGRESS}$ for that calculation region ranks relative to (is greater or smaller than) $\Delta I_{INGRESS}$ for all other calculation regions. A third numeric rank that corresponds to $\Delta T_{MVASCULAR}$ is generated based on how $\Delta T_{MVASCULAR}$ for that calculation region ranks relative to (is longer or shorter than) $\neq\neq T_{MVASCULAR}$ for all other calculation regions. A fourth numeric rank that corresponds to $\Delta T_{VENOUS}$ is generated based on how $\Delta T_{VENOUS}$ for that calculation region ranks relative to (is longer or shorter than) $\Delta T_{VENOUS}$ for all other calculation regions. For example, a higher numeric rank may be assigned to a pixel having higher $\Delta I_{INGRESS}$. As another example, a lower rank may be assigned to a pixel having a slower $\Delta T_{ONSET}$. The set of numeric ranks for that calculation region comprises these four numeric ranks corresponding to the four parameters. This process is repeated for each calculation region, such that each calculation region has an associated set of numeric ranks corresponding to the parameters. The range of possible values for the numeric ranks may correspond to the number of parameter types being summed to generate the total rank value, weighting factors, and/or a display scale range (e.g., 8-bit gray scale range) for the total rank value, as described further below. In other variations, any suitable kind and/or number of parameters may be used to quantify the time-intensity curves. For instance, each set of numeric ranks may by based on the ranking of only subset (e.g., only two or three) of the four parameters described in this paragraph.

Generating the total rank value for each calculation region 118 may include summing two or more (e.g., all) of the individual numeric ranks (subranks) on a calculation region-by-calculation region basis, such that every calculation region has a total rank value based on the summation of two or more (e.g., all) of its numeric rank values. In some variations, the summation of the set of numeric values may include the steps of Formula 1:

$$R_{Total} = wt_1 * R_1(\Delta I_{INGRESS}) + wt_2 * R_2(\Delta T_{ONSET}) + wt_3 * R_3(\Delta T_{MVASCULAR}) + wt_4 * R_4(\Delta T_{VENOUS})$$ Formula 1:

where $R_{Total}$ is the total rank value; $wt_n$ is a weighting factor applied to a corresponding parameter (e.g., $wt_1$ applied to $\Delta I_{INGRESS}$), $wt_2$ applied to $\Delta T_{ONSET}$, $wt_3$ applied to $\Delta T_{MVASCULAR}$, and $wt_4$ applied to $\Delta T_{VENOUS}$); and $R_n$ (parameter) is the subrank for the denoted parameter (e.g., $R_1(\Delta I_{INGRESS})$ is the numerical rank for ($\Delta I_{INGRESS}$), $R_2(\Delta T_{ONSET})$ is the numerical rank for $\Delta T_{ONSET}$, $R_3(\Delta T_{MVASCULAR})$ is the numerical rank for $\Delta T_{MVASCULAR}$, and $R_4(\Delta T_{VENOUS})$ is the numerical rank for $\Delta T_{VENOUS}$).

After each of the selected parameters (e.g., $\Delta I_{INGRESS}$, $\Delta T_{ONSET}$, $\Delta T_{MVASCULAR}$, $\Delta T_{VENOUS}$) is measured, a subrank value is assigned to each of the selected parameters and is within a selected range of values. In some variations, the subrank value may be within a range of values that depends at least in part on the weighting factors applied to the selected parameters and a selected range of values for $R_{Total}$. In some variations, the weighting factors are approximately equal. For example, in one exemplary implementation of Formula 1, each of the weighting factors may be approximately equal (e.g., $wt_1 = wt_2 = wt_3 = wt_4$) and the range of values for $R_{Total}$ may be approximately 0-255 which corresponds to an 8-bit gray scale. In this example, each of the parameters is associated with a subrank value from 0-63 (e.g., $R_1=0$ to 63, $R_2=0$ to $6_3$, $R_3=0$ to 63, $R_4=0$ to 63; subrank $(R_1, R_2, R_3, R_4) \in [0 \ldots 63])$, which is approximately one-quarter of the 8-bit gray scale. In other variations, the weighting factors, the range for total rank values, or both, may differ.

Formula 2 is an example of a particular implementation of Formula 1:

$$R_{Total} = \text{Max}(\text{MAX\_RANK}, \Delta I_{INGRESS}) + \\ (\text{MAX\_RANK} - \text{Min}(\text{MAX\_RANK}, \Delta T_{ONSET})) + \\ (\text{MAX\_RANK} - \text{Min}(\text{MAX\_RANK}, \Delta T_{MVASCULAR})) + (\text{MAX\_RANK} - \text{Min} \\ (\text{MAX\_RANK}, \Delta T_{VENOUS}))$$ Formula 2:

where MAX_RANK is the maximum numeric rank value for the denoted parameter across all calculation regions. For example, MAX_RANK may be 63, and each parameter value may range 0-63, inclusive.

In a second variation of generating a total rank value 118, the total rank value may be generated by mapping a set of numeric metrics for each calculation region with a hash function. This results in a unique total rank value for each calculation region. In some versions, the numeric metrics for each calculation region may be numeric ranks generated as described in the first variation of generating a total rank value (e.g., assigning numeric ranks to different parts of the time-intensity curve for that calculation region). For example, if the curve fitting were to be represented as a cubic polynomial such as $f(x) = C_1 + C_2 X + C_3 X^2 + C_4 X^3$, then the numbers can be combined in a single rank. Therefore, the total rank value, $R_{Total}$, would be a combination $R_{Total} = [C_1, C_2, C_3, C_4]$ and derived according to any of the various variations described herein (e.g, elegant pairing). In some versions, the numeric metrics for each calculation region may correspond to coefficients of the polynomial that best fits the time-intensity curve for that calculation region. In some versions, the numeric metrics may be measured intensity values of the time-intensity curve at pre-defined intervals. In other versions, the numeric metrics may be based on other suitable one or more parameters, which may be different for different imaging modalities.

The hash function uniquely maps each set of numeric metrics to a single number. For example, the hash function may be a Cyclic Redundancy Check. As another example, the hash function may be a pairing function that maps pairs of numbers to a single number, such as Cantor's Pairing or Elegant Pairing. In versions in which the hash function is a pairing function, the hash function can be applied recursively, pairing by pairing, until all the numeric metrics have been encoded as a single value (total rank value) for each calculation region. A pairing function is a process to uniquely encode two natural numbers into a single natural number, in such a way that is also strictly monotone in each of its arguments. For example, if P: N×N→N is a pairing function, then for all x, y∈N P (x, y)<P (x+1, y) and P(x, y)<P (x, y+1). Apart from uniqueness and being monotone, the function should be easily generalized to higher dimensions. Namely, it may be possible to map multiple parameters (e.g., three, four, and more parameters, etc.) into a single number. One exemplary candidate that meets these criteria is a so called Elegant Pairing function which may be defined as follows (Formula 3):

$$ElegantPair[x_-, y_-] := \begin{cases} y^2 + x & x \neq \text{Max}[x, y] \\ x^2 + x + y & x = \text{Max}[x, y] \end{cases} \quad \text{Formula 3}$$

To pair more than two numbers, pairings of pairings can be used. For example, f (i,j,k) can be defined as P(i,P(j,k)) or P(P(i,j),k)), but f (i,j,k,l) should be defined as P(P(i,j), P(k,l)). Once we create set of numbers representing the ranks, we may scale them as needed (e.g., 0 to 255)

The algorithms described in connection with the first and second variations of generating a total rank value are exemplary only. In other variations, such as for different applications or imaging modalities, the method may additionally or alternatively include performing other suitable algorithms for generating a total rank value based on comparing two or more (e.g., all) of the sets or parameter values for the plurality of calculation regions.

Converting the Total Rank Values for the Calculation Regions into a Ranking Map Image As shown in FIG. 1, the method includes converting the total rank values into a ranking map image 120. The resulting ranking map image visualizes the spatial distribution of total rank values across the calculation regions, and thereby visualizes any relative differences in total rank values among the calculation regions. Thus, the ranking map image shows any relative differences among different parts of the imaged tissue with respect to the selected parameters, which highlights different properties (e.g., physiological properties) of the tissue in an objective, easily understood manner. As further described above, as a result, the ranking map image may facilitate more effective, consistent clinical assessments and decision-making.

In some variations, converting the total rank values into a ranking map image 120 may include correlating each total rank value to an intensity value, such that the calculation regions in the ranking map image may be depicted with varying intensity values corresponding to total rank values. The conversion may involve assigning a display brightness value to each total rank value wherein the total rank value and brightness value are in a direct relationship (e.g., the higher the rank, the higher the pixel's intensity). The direct relationship may be linear or nonlinear. In other variations, the conversion may be based on an indirect relationship between the total rank value and brightness value.

In some variations, the total rank value may be mapped to a gray scale or a color scale value. For example, the total rank values may be mapped to an 8-bit grayscale display value (e.g., from 0 to 255), allowing for a grayscale image representation of the total rank values. In some variations, to optimize visual perception, a color scheme can be applied to the grayscale image representation with different grayscale value ranges represented in appropriately contrasting colors (such as a false color or pseudo color). Other scales may additionally or alternatively be applied to convert the total rank values into pixel values for the spatial ranking map image, such that the differences in pixel values reflect the relative differences in total rank values and among different regions of the imaged tissue.

Displaying the Ranking Map Image and Other Steps

In some variations, as shown in FIG. 1, the method may further include displaying the ranking map image on a display 122. For example, the ranking map image may be displayed within a user interface on a video monitor in a fluorescence imaging system, or other suitable display. The ranking map image may be displayed alone, or in combination with another image (e.g., overlaid with or superimposed on an anatomical image) or other data. Such other data may relate, for example, to a systemic or local condition of the subject providing a particular clinical context for that subject. Such a condition may comprise a comorbid condition including, for example, hypertension, dyslipidemia, diabetes mellitus, chronic obstructive pulmonary disease, coronary artery disease, chronic kidney disease, or a combination thereof. In some variations, the ranking map image may be displayed with a wound index value characterizing a wound in the tissue, as described further below.

In some variations, the method may further comprise correlating the map of total rank values with a risk estimate for clinically relevant (e.g., tissue perfusion-related) condition. Such assessments may be made pre-intervention, during treatment/procedure, and post-intervention. The method may also comprise defining a diagnosis to identify and characterize a clinically relevant (e.g., tissue perfusion-related) condition in the subject pre-intervention, during treatment/procedure, and post-intervention. In other variations, the method may exclude the correlation and diagnoses steps.

Method for Characterizing a Wound

Figure 4:
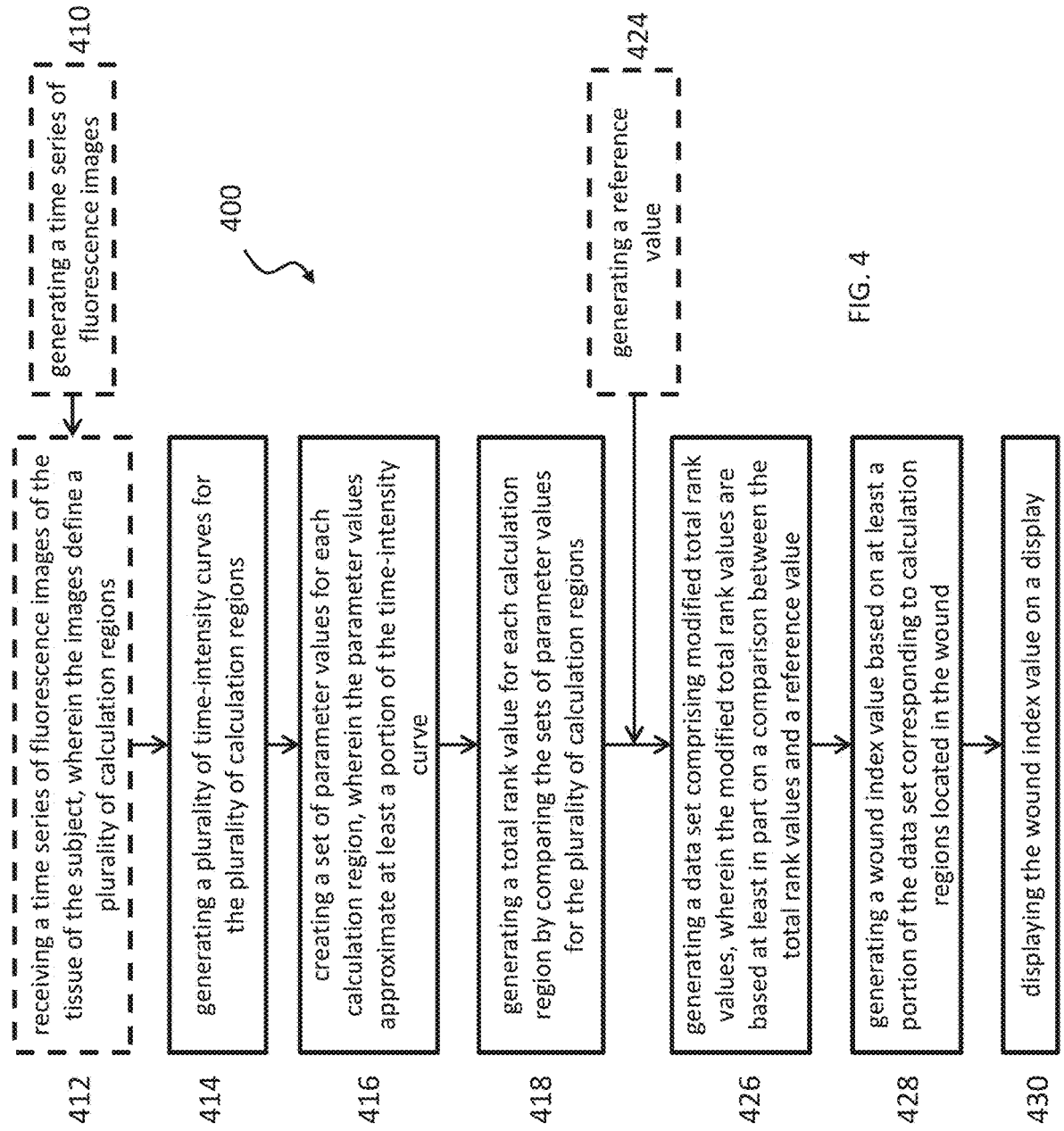
FIG. 4 is an illustrative block diagram of an exemplary method for characterizing a wound in a target tissue region of a subject.

The method 100 described above for characterizing tissue of a subject may serve as a foundation for further applications of the processed image data. For example, as shown in FIG. 4, an exemplary method 400 for use in medical imaging for characterizing a wound in a target tissue region of a subject may include: receiving a time series of fluorescence images of the target tissue region of the subject 412, wherein the images define a plurality of calculation regions, generating a plurality of time-intensity curves for the plurality of calculation regions 414, creating one or more parameter values for each calculation region 416, wherein the one or more parameter values approximates at least a portion of the time-intensity curve, generating a total rank value for each calculation region by comparing the sets of parameter values for the plurality of calculation regions 418, generating a data set comprising modified total rank values 426, wherein the modified total rank values are based at least in part on a comparison between the total rank values and a reference value, and generating a wound index value 428 based on at least a portion of the data set corresponding to calculation regions located in the wound. In some variations, the method 400 may further include generating the time series of fluorescence images 410, and/or displaying the ranking map image on a display 430.

Generally speaking, the method 400 may be performed with respect to a wound that represents a deviation from the reference value. The wound may include any kind of chronic or acute injury to tissue, such as an incision, a pressure ulcer, a venous ulcer, an arterial ulcer, a diabetic lower extremity ulcer, a laceration, an abrasion, a puncture, a contusion, an avulsion, a cavity, a burn, a combination thereof, and/or the like. Furthermore, the wound may be caused by one or more of various trauma events and/or medical conditions, such crush wounds, battle wounds (e.g., gunshot/explosion), or wounds resulting from gangrene, inflammation, venous stasis, lymphedema, etc.

One challenge in wound management is that the medical condition or nature of a wound can be viewed differently among clinicians depending, for example, on the skill and experience of the clinician. Currently wound management techniques may provide information about the wound's pathological history, but fail to provide reliable indicators of viability and/or restorative potential (e.g., whether wound and/or periwound is likely to develop complications, is capable of healing, how healing progresses, and whether the treatment applied is effective and when it can be discontinued). Furthermore, wounds exist where no pathology is demonstrable by conventional techniques.

Currently, in an attempt to address some of these challenges, some fluorescence imaging technology may, in addition to providing a visual display, generate metrics from the video data in order to numerically characterize the blood flow and/or perfusion in and around the wound, and thereby attempt to reduce subjectivity and perception biases in assessing the tissue perfusion status. However, such a numeric characterization is not informed by an understanding of the underlying biological mechanisms of wound healing, which is necessary in order to convey information which would allow clinicians to make clinically meaningful assessments. More specifically, a comprehensive understanding of blood flow and/or tissue perfusion dynamics during the wound healing process would be extremely helpful for such image data to yield an accurate interpretation of wound healing status. Existing fluorescence imaging technologies do not incorporate such knowledge and subsequently fail to support a standardized protocol for assessing blood flow and/or tissue perfusion, and fail to provide accurate characterization and classification of blood flow/perfusion behavior in the tissue that is sufficiently consistent between clinicians, between patients, and between multiple imaging sessions.

In one variation, the method described herein relates to medical imaging technology for characterizing a wound in a target tissue region (e.g., wound, periwound). The method may facilitate segregation and selection of data of interest in connection with the target tissue region (e.g., data in the target tissue region arising from the wound region only), while suppressing the remaining data of less interest (e.g., data in the target tissue arising from tissue other than wound tissue). In this manner, the method provides enhanced diagnostic power by minimizing any dilution of the information of interest. Moreover, the method provides a consistent objective, quantitative representation of the state of the target tissue (e.g., wound or periwound) that is not subject to biases of perception and/or skill of a clinician. Furthermore, the method may provide a reliable and consistent way to compare and track wound healing status (e.g., based on blood flow and/or perfusion) of a patient over time across multiple imaging sessions. Thus, the method may enable a more accurate, consistent, and quantitative assessment of the target tissue region, as well as targeted formulation of clinical care strategies (e.g., recommending treatments, monitoring of treatment efficacy, determining if/when the treatment should be discontinued, formulating surgical strategy). Ultimately, the method also may facilitate decreasing patient risk for patients who are sensitive to medication, and decreasing the total cost of procedure and/or treatment.

Assessing a wound according to the various embodiments encompasses the assessment of perfusion dynamics. For example, the methods and systems described herein are applicable to other clinical applications such as, for example, pre-surgical evaluation of patients undergoing plastic reconstruction procedures, general surgical procedures involving tissue reapproximation with vascular anastomoses (e.g., skin flap transfers, colon reconstruction, etc.) or assessment of viability and function of cardiac tissue during cardiac surgery. Furthermore, the methods and systems described herein are further applicable to a clinical evaluation of any dynamic process, such as for example tissue perfusion or other dynamic behavior of an imaging agent in tissue, that can be represented by a spatial map of image data generated from a time series of input data (e.g., image frames) that exhibit the process, and further by a wound index generated from data in the spatial map.

In one application of the method, the data derived from performing the method and using the system described herein can provide predictive information to the clinician by correlating the data with the process of angiogenesis, which refers to a naturally occurring process of blood vessel growth and regression, and it occurs as an integral component of tissue repair and regeneration. Angiogenesis increases in healing, then is pruned to physiological baseline. For example, during wound healing, sprouting and branching of vessels results in an extensive but immature and leaky neovascular network that eventually resolves by systematic pruning of extraneous vessels to yield a stable, well-perfused vascular network that maintains tissue homeostasis (for example see *Mechanisms of Vessel Regression: Toward an Understanding of the Resolution of Angiogenesis*, Mateusz S. Wietecha et al., *Current Topics in Microbiology and Immunology*, 2013, 367:3-32). FIG. 5A schematically illustrates what is understood in the art to be a normal wound healing process. In contrast, FIG. 5B schematically illustrates what is understood in the art to be a chronic wound healing process. In chronic wounds, angiogenesis is out of balance. When such chronic wounds are imaged using fluorescence imaging, hyperfluorescence is observed, which is believed to occur as a result of vessel "leakiness" in such wounds (for example see *Expression and Proteolysis of Vascular Endothelial Growth Factor is Increased in Chronic Wounds*, Gereon Lauer et al., *J Invest Dermatol* 115:12-18, 2000; *Vascular Endothelial Growth Factor Is a Secreted Angiogenic Mitogen,* David W. Leung et al., Science, Vol. 246, p. 1306, Dec. 8, 1989). Therefore, according to an embodiment, a correlation of the methods of the present invention with the process of angiogenesis can facilitate or guide clinical decision-making by allowing wound microcirculation monitoring. By using the method and systems described herein, depending on where in the process of angiogenesis the wound healing is determined to be during an initial assessment, a clinician is able to determine, for example, where the subsequent reading should fall if the treatment applied is effective. The data derived from performing the method and using the systems described herein yet further facilitates distinguishing between multiple wound regions in the target tissue which may develop, progress and/or heal according to different time lines.

Although the methods and systems described herein facilitate a quantitative assessment of the wound that may be used alone, such a quantitative assessment may also be used in combination with a qualitative assessment and/or indicator (e.g., a systemic or local indicators relating to a patient's condition) to provide enhanced diagnostic power to the clinician.

Additionally, although variations of the method are described herein in the context of a time series of fluorescence images for the prognostic assessment of wounds, the method may be applied to other sources of input data generated as a time series which relate to a dynamic behavior of an imaging agent in the tissue and for other clinical purposes where the target tissue comprises regions with differing tissue properties. Examples can include detection of fluorescence from an excited imaging agent, as well as other sources of input data, such as a time series of images generated by detection of absorption associated with an imaging agent.

In some variations, the steps of generating the time series of fluorescence images 410, receiving the time series of fluorescence image 412, generating a plurality of time intensity curves 414, creating one or more parameter values for each calculation region 416, and/or generating a total rank value for each calculation region 418 are similar to the steps 110, 112, 114, 116, and 118 described above with respect to the method 100 for characterizing tissue of a subject.

Generating a Data Set Comprising Modified Total Rank Values

As shown in FIG. 4, the method 400 for characterizing a wound may include generating a data set comprising modified total rank values 426. In some variations, the step of generating a data set comprising modified total rank values includes modulating at least a portion of the total rank values and/or comparing the total rank values against a reference value.

Modulating at least a portion of the total rank values enhances or exaggerates the differences between total rank values corresponding to the wound regions of the target tissue and total rank values corresponding to the non-wound regions of the target tissue and other areas of less interest. In other words, modulating at least some of the total rank values facilitates selection of the data of interest (e.g., data arising from the wound in the target tissue) from other data (e.g., data not arising from the wound region in the target tissue and/or data associated with background).

In some variations, the modulation may include modulating a first portion of the total rank values with a first modulation function to generate a first modulated data set, and modulating a second portion of the total rank values with a second modulation function to generate a second modulated data set. The first modulated data set may include modified total rank values that correspond to the wound, and therefore may be considered wound characterization values. The second modulated data set may include modified total rank values that correspond to non-wound regions, and therefore may be considered non-wound characterization values.

The first and second modulation functions may be distinct. For instance, in one variation, the first modulation function may be an identity function (which returns the same value as the input) such that the total rank values in the first modulated data set are unchanged, and the second modulation function may cause the total rank values in the second modulated data set to equal zero. For example, where R=the unmodified total rank value, the first modulation function M1 may be M1(R)=R and the second modulation function M2 may be M2(R)=0. As another example, the first modulation function may be M1(R)=R if R>Ref+Tolerance, where Tolerance is a selected, defined value. As another example, the first modulation function may be M1(R)=R-Hypo for the hypo-perfused areas within the imaged tissue, where R-Hypo is a pre-defined numeric total rank value that is not equal to the total rank values for areas associated with the hyper-fluorescing wound.

In some variations, the modified total rank values may be converted into a modified ranking map image. For example, each of the modified total rank values may be correlated to an intensity value, such that the calculation regions in the modified ranking map image may be depicted with varying intensity values corresponding to the modified total rank values. In another example, each of the modified total rank values may be correlated to a grayscale or color scale value. In such a modified ranking map image, modified total rank values corresponding to wounded regions will appear significantly different from modified total rank values corresponding to non-wounded regions, due to the numerical distance between them following modulation. This modified ranking map image may be displayed, such as on video monitor in an imaging system or other suitable display.

Comparing the modified total rank values against a reference value further isolates the data corresponding to the wound regions of the target tissue from data corresponding to non-wounded regions of the target tissue. In some variations, the comparison step may include subtracting the reference value from all the modified total rank values for all calculation regions, thereby leaving total rank values corresponding to a precise outline of the wound in the target tissue. In other variations, where the step of comparing against a reference value is performed before the step of modulating the total rank values, the comparing step involves subtracting the reference value from all the unmodified total rank values.

In some variations, as shown in FIG. 4, the method may include generating a reference value 424 for use in modifying the total rank values. The reference value may be generated according to any of a number of approaches. For example, the reference value may be derived from a time series of reference images or other input data (e.g., a time series of reference fluorescence images) obtained from a reference tissue. The reference tissue may be the tissue of: a healthy subject; a population of healthy subjects; a healthy tissue region in the target tissue of the subject; a healthy tissue region outside the target tissue of the subject; a combination of two or more of such alternatives; or a further combination of such alternatives taking into account the background in the time series of reference images.

Furthermore, the reference value may be specific for a particular modality, a condition, a clinical context or a combination of these factors within which the wound is being assessed. Thus for example, the reference value may be derived from a time series of reference images obtained from reference tissue of: a healthy tissue region in the target tissue of the subject or a population of subjects presenting a particular modality or a condition (e.g., a systemic condition such as diabetes); or a healthy tissue region outside the target tissue of the subject or a population of subjects presenting a particular modality or a condition (e.g. a systemic condition such as diabetes); a combination of such alternatives; or a further combination of such alternatives taking into account the background in the time series of reference images.

In one variation, the reference value may be based on reference total rank value, which may be calculated in a manner similar to total rank values described above. For instance, a time series of reference images or other input data may be obtained from reference tissue and serve as the basis for a reference time-intensity curve that is generated for a reference calculation region. Subsequently, a reference rank value for the reference calculation region may be generated or assigned based on one or more parameters selected to approximate the reference time-intensity curve. The reference calculation region for a particular subject or a population of subjects may be selected manually, or may be selected by the processor with or without assistance from the operator. The time series of reference images may be acquired before, substantially simultaneously, or after acquisition of the time series of images for the target tissue.

In another variation, the reference value is not derived from a separate time series of reference images, but instead may be equal to the background intensity or other metric in a time series of images (e.g., fluorescence images) from the target tissue. In yet another variation, the reference value is based on a combination of a separate time series of reference images or other input data, and the time series of fluorescence images or other input data.

In some variations, the reference value can be modified by a modifier such as a tolerance value, a multiplier, or a combination thereof. For example, the modifier may be one or more reference values taken from another site of a subject or a group/population of subjects, or an average of such reference values. The modifier may compensate for measurement errors in calculation of the reference rank. In various other embodiments, the reference value may be further modified by being divided by one or more other reference values.

A plurality of reference values may be assembled in a table or a database (e.g., an atlas) for a particular subject or a population of subject, a particular application, modality, condition or clinical context. Such a table or database may then be used to provide the reference value.

Generating a Wound Index Value

As shown in FIG. 4, the method 400 also includes generating a wound index value 428 based on at least a portion of the data set of modified total rank values. In some variations, this wound index value is generally a single, numerical value. In some variations, the wound index value is based on an average of the wound characterization values. For example, generating a wound index value may include summing the modified rank values corresponding to calculation regions located in the wound, and dividing the sum by the total number of pixels in the image (i.e., averaging over the entire image). As another example, generating a wound index value may include summing the modified rank values corresponding to calculation regions located in the wound, and dividing the result by the number of pixels representing the tissue portion of the image that excludes the background (i.e., averaging over the tissue portion of the image).

The generated wound index value provides a quantitative representation of the wound. According to an embodiment, the wound index value represents wound activity (i.e., a wound activity value). The wound index value may be tracked over time, which may be represented in a graph form which facilitates deriving information about the rate and slope. A graph representation of the wound index value over time facilitates an evaluation of a change in the wound index value over time, which in some embodiments is indicative of a change in a state or activity of the wound over time. Examples of the state or activity of the wound include a property of the wound, a condition of the wound, healing status of the wound (e.g., inflammation, malignancy, abnormality, disease). Tracking the wound index value over time facilitates tracking the rate of change which, for example, may be correlated with the stages of the wound healing. Tracking the wound index value over time may further be correlated with the angiogenesis curve. This finding may subsequently be correlated with the stage of healing the patient is in. Furthermore, information relating to a change in the wound index value over time provides predictive information regarding the point at which a treatment, such as hyperbaric oxygen therapy, negative pressure therapy, or other known wound care therapies, may be stopped without compromising the healing process. As a result, the wound index value provides for an objective, standardized protocol for assessing tissue blood flow and/or tissue perfusion, which may facilitate a way to reliably and consistently compare and track blood flow and/or perfusion status of a patient over time across multiple imaging sessions, regardless of the clinician performing the assessment.

Displaying the Wound Index Value and Other Steps

In some variations, as shown in FIG. 4, the method 400 may further include displaying the wound index value on a display 430. For example, the wound index value may be displayed within a user interface on a video monitor in a fluorescence imaging system, or other suitable display. In some variations, the wound index value can be used alone or in combination with a visualization of the other steps of the method of the present invention to enhance the information conveyed to the clinician (which facilitates enhanced diagnostics), which may further be overlaid over an anatomical image and/or correlated with other data or information regarding the patient (e.g., a systemic condition of the patient). For example, in some variations, the wound index value may be displayed alone or in combination with the unmodified and/or modified total rank values (e.g., ranking map image or modified ranking map image). As another example, the wound index value may be displayed in combination with a maximum perfusion map and/or other suitable maps or images. In some variations, the data set of modified total rank values may be correlated with a risk estimate for clinically relevant (e.g., perfusion-related) condition. Such assessments may be made pre-intervention, during treatment/procedure, and/or post-intervention. The method may also further comprise defining a diagnosis to identify and characterize a clinically relevant (e.g., perfusion-related) condition in the subject pre-intervention, during treatment/procedure, and post-intervention. In various other embodiments, the method may exclude the correlation and/or diagnoses steps.

In some variations, machine learning may additionally or alternatively be used to generate both the ranking map, the wound index value, and/or to reveal blood flow and/or tissue perfusion patterns. In some variations, the wound index value may be used as input into a machine learning process (getting a processor or a computer to act without being explicitly programmed), deep machine learning, data mining, and/or pattern recognition where the machine learning is then subsequently used for assessment of a time series of input data or an image of tissue such as a wound. Furthermore, the time series of images or other input data, the ranked calculation regions (e.g., a ranked image or a portion thereof) or a combination thereof may be used as input for a machine learning processor, and processed or classified according to the learning conducted by the machine learning processor using the initial input wound index values (e.g., wound activity index values).

The various aspects of the method are further illustrated in the Examples section with application to various clinical contexts.

Systems for Characterizing Tissue

A system for characterizing tissue of a subject (e.g., characterizing a wound of a target tissue region of a subject) includes one or more processors and memory having instructions stored thereon, wherein the instructions when executed by the one or more processors cause the system to perform the methods substantially as described above for characterizing tissue and/or characterizing a wound in a target tissue region of a subject.

In some variations, the system for characterizing tissue of a subject is a fluorescence imaging system. FIG. 6 is a schematic example of a fluorescence imaging system 610. The fluorescence imaging system 610 comprises a light source 612 to illuminate the tissue of the subject to induce fluorescence emission from a fluorescence imaging agent 614 in the tissue of the subject (e.g., in blood), an image acquisition assembly 616 configured to generate the time series of fluorescence images from the fluorescence emission, and a processor assembly 618 configured to process the generated time series of fluorescence images according to any of the variations of the methods described herein. The processor assembly 618 may include memory 668 with instructions thereon, a processor module 662 configured to execute the instructions on memory 668 to process the time series of fluorescence images as described in connection with the various embodiments of the methods described above, and a data storage module 664 to store the unprocessed and/or processed time series of fluorescence images. In some variations, the memory 668 and data storage module 664 may be embodied in the same storage medium, while in other variations the memory 668 and the data storage module 664 may be embodied in different storage mediums. The system may further include a display 666 on which to display images and other data, such as some or all of the time series of fluorescence images or other input data, a ranking map image, and/or a wound index value.

In some variations, the light source 612 includes, for example, an illumination module 620. Illumination module 620 may include a fluorescence excitation source configured to generate an excitation light having a suitable intensity and a suitable wavelength for exciting the fluorescence imaging agent 614. As shown in FIG. 7, the illumination module 620 may comprises a laser diode 722 (e.g., which may comprise, for example, one or more fiber-coupled diode lasers) configured to provide an excitation light to excite the fluorescence imaging agent (not shown) in tissue of the subject. Examples of other sources of the excitation light which may be used in various embodiments include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

Referring again to FIG. 6, in some variations, the light output from the light source 612 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 616. The fluorescence excitation source may be selected to emit at a wavelength close to the absorption maximum of the fluorescence imaging agent 14 (e.g., ICG, etc.). For example, as shown in FIG. 7, the output 724 from the laser diode 722 may be passed through one or more focusing lenses 726, and then through a homogenizing light pipe 728 such as, for example, light pipes commonly available from Newport Corporation, USA. Finally, the light may be passed through an optical diffractive element 732 (i.e., one or more optical diffusers) such as, for example, ground glass diffractive elements also available from Newport Corporation, USA. Power to the laser diode 722 may be provided by, for example, a high-current laser driver such as those available from Lumina Power Inc. USA. The laser may optionally be operated in a pulsed mode during the image acquisition process. An optical sensor such as a solid state photodiode 730 may be incorporated into the illumination module 620 and may sample the illumination intensity produced by the illumination module 620 via scattered or diffuse reflections from the various optical elements. In some variations, additional illumination sources may be used to provide guidance when aligning and positioning the module over the area of interest.

Referring again to FIG. 6, in some variations, the image acquisition assembly 616 may be a component of a fluorescence imaging system 610 configured to acquire the time series of fluorescence images from the fluorescence emission from the fluorescence imaging agent 614. The image acquisition assembly 616 may include a camera module 640. As shown in FIG. 8, the camera module 640 may acquire images of the fluorescence emission 842 from the fluorescence imaging agent in the tissue by using a system of imaging optics (e.g., 846*a*, 846*b*, 848 and 850) to collect and focus the fluorescence emission onto an image sensor assembly 844. The image sensor assembly 844 may comprise at least one 2D solid state image sensor. The solid state image sensor may be a charge coupled device (CCD), a CMOS sensor, a CID or similar 2D sensor technology. The charge that results from the optical signal transduced by the image sensor assembly 844 is converted to an electrical video signal, which includes both digital and analog video signals, by the appropriate read-out and amplification electronics in the camera module 840.

According to an exemplary embodiment of a fluorescent imaging system, the light source may provide an excitation wavelength of about 800 nm+/−10 nm, and the image acquisition assembly uses emission wavelengths of >820 nm with NIR-compatible optics for, for example, ICG fluorescence imaging. In an exemplary embodiment, the NIR-compatible optics may include a CCD monochrome image sensor having a GigE standard interface and a lens that is compatible with the sensor with respect to optical format and mount format (e.g., C/CS mount).

In some variations, the processor module 662 comprises any computer or computing means such as, for example, a tablet, laptop, desktop, networked computer, or dedicated standalone microprocessor. For instance, the processor module 662 may include one or more central processing units (CPU). In an exemplary embodiment, the processor module 662 is a quad-core, 2.5 GHz processor with four CPUs where each CPU is a microprocessor such as a 64-bit microprocessor (e.g., marketed as INTEL Core i3, i5, or i7, or in the AMD Core FX series). However, in other embodiments, the processor module 662 may be any suitable processor with any suitable number of CPUs and/or other suitable clock speed.

Inputs for the processor module 662 may be taken, for example, from the image sensor 844 of the camera module 640 shown in FIG. 8, from the solid state photodiode 730 in the illumination module 620 in FIG. 7, and/or from any external control hardware such as a footswitch or remote-control. Output is provided to the laser diode driver and optical alignment aids. As shown in FIG. 6, in some variations, the processor assembly 618 may have a data storage module 664 with the capability to save the time series of images, or data representative thereof, or other input data to a tangible non-transitory computer readable medium such as, for example, internal memory (e.g. a hard disk or flash memory), so as to enable recording and processing of acquired data. In some variations, the processor module 662 may have an internal clock to enable control of the various elements and ensure correct timing of illumination and sensor shutters. In some variations, the processor module 662 may also provide user input and graphical display of outputs. The fluorescence imaging system may optionally be configured with a video display 666 or other monitor to display the time series of fluorescence images as they are being acquired or played back after recording. The video display 666 may additionally or alternatively visualize data generated during performance of the methods described herein, such as a ranking map image and/or wound index value.

In operation of the exemplary system described in FIGS. 6-8, the subject is positioned relative to fluorescence imaging system 610 such that an area of interest (e.g., target tissue region) is located beneath the light source 612 and the image acquisition assembly 616 such that the illumination module 620 of light source 612 produces a substantially uniform field of illumination across substantially the entire area of interest. In some variations, prior to the administration of the fluorescence imaging agent 614 to the subject, an image may be acquired of the area of interest for the purposes of background deduction. To acquire fluorescence images, the operator of the fluorescence imaging system 610 may initiate the acquisition of the time series of fluorescence images by depressing a remote switch or foot-control, or via a keyboard (not shown) connected to the processor assembly 618. As a result, the light source 612 is turned on and the processor assembly 618 begins recording the fluorescence image data provided by the image acquisition assembly 616. When operating in the pulsed mode of the embodiment, the image sensor 844 in the camera module 640 is synchronized to collect fluorescence emission following the laser pulse produced by the diode laser 722 in the illumination module 620. In this way, maximum fluorescence emission intensity is recorded, and signal-to-noise ratio is optimized. In this embodiment, the fluorescence imaging agent 614 is administered to the subject and delivered to the area of interest via arterial flow. Acquisition of the time series of fluorescence images is initiated, for example, shortly after administration of the fluorescence imaging agent 614, and the time series of fluorescence images from substantially the entire area of interest is acquired throughout the ingress of the fluorescence imaging agent 614. The fluorescence emission from the region of interest is collected by the collection optics of the camera module 640. Residual ambient and reflected excitation light is attenuated by subsequent optical elements (e.g., optical element 850 in FIG. 8 which may be a filter) in the camera module 640 so that the fluorescence emission can be acquired by the image sensor assembly 844 with minimal interference by light from other sources.

In some variations, following the acquisition or generation of the time series of fluorescence images, the processor assembly 618 (e.g., processor module 662 or other processor) may then be initiated to execute instructions stored on memory 668 and perform one or more methods as described herein. The system 610 may visualize on display 666 the ranking map and/or any clinical correlations or diagnosis derived therefrom or both may be displayed to the user as, for example, a grayscale or false color image, and/or stored for subsequent use. Additionally or alternatively, the system 610 may display on display 666 a wound index value.

In some variations, the system for characterizing tissue or characterizing a wound in a target tissue region comprises a user interface, a processor configured to communicate with the user interface, and a non-transitory computer-readable storage medium having instructions stored which, when executed by the processor, cause the processor to perform one or more of the methods for characterizing tissue and/or characterizing a wound in the tissue described herein. In some variations, the processor may be a component of the imaging system. In other variations, the processor may be located remotely from and in communication with an imaging system, where the imaging system may be the fluorescence imaging system described above, or any suitable imaging system.

A tangible non-transitory computer readable medium having computer-executable (readable) program code embedded thereon may provide instructions for causing one or more processors to, when executing the instructions, perform one or more of the methods for characterizing tissue and/or characterizing a wound in the tissue described herein. Program code can be written in any appropriate programming language and delivered to the processor in many forms, including, for example, but not limited to information permanently stored on non-writeable storage media (e.g., read-only memory devices such as ROMs, CD-ROM disks, etc.), information alterably stored on writeable storage media (e.g., hard drives or the like), information conveyed to the processor through communication media, such as a local area network, a public network such as the Internet, or any type of media suitable for storing electronic instruction. When carrying computer readable instructions that implement the various embodiments of the method of the present invention, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods for characterizing tissue and/or characterizing a wound in the tissue described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein.

EXAMPLES

In some of the examples described below, "maximum perfusion map" refers to a map created by assigning each pixel in the calculation region of the time series of fluorescence input images the value of its maximum intensity reached during the entire measurement period.

Perfusion dynamics for every pixel in a selected calculation region of an image (i.e., a region of interest for which to perform the ranking analysis) in a time series of fluorescence input images can be characterized by the shape of its angiographic curve. The curves can be classified based on some pre-defined criteria, and as a result, every pixel can be assigned a rank corresponding to the type of curve it exhibits. When near-infrared imaging technology is applied for blood flow visualization in chronic wounds, as illustrated in the examples below, the great majority of the wounds exhibit the so called hyper-fluorescence effect. The area around the wound may show very fast rate of ICG (or other imaging agent) influx resulting in higher-than-average intensity reached by its pixels. This effect appears to be exclusive to wounds and does not appear to occur in healthy tissue. A plurality of the total rank values for each case was visualized in a ranking map image, which in the context of the examples may be referred to interchangeably as "a wound activity map." As described in further detail above along with other advantages of a ranking map image, one purpose of a wound activity map is to provide an easy way of visualization of the blood flow patterns forming in and around a wound.

As is illustrated in some of the examples below, the wound index value (WIV) generated from the comparison of each of the rank values with a reference value further enhances the qualitative wound care assessment via the wound activity map to provide a quantification tool for tracking the wound and the wound treatment progress. As was described above, the formation of new vessels during the healing or tissue regeneration is known as angiogenesis, and is accompanied by the growth of high-density vessels network around the wound, which results in increased blood supply to the damaged tissue. As the wound heals, the excessive blood vessels are gradually trimmed down until the normal structure of vasculature is restored. The wound index values may appear to possibly correlate with the angiogenesis process, for both normal and chronic wounds, and facilitate providing a meaningful way of quantifying the wound healing progress. In particular, the wound index values provide an objective, consistent way to compare and track wound healing status (e.g., based on blood flow and/or tissue perfusion) of a patient over time across multiple imaging sessions. As described in further detail above, the WIV enables characterization and classification of blood f low/perfusion behavior in and around a wound that is sufficiently consistent between clinicians, between patients, and between multiple imaging sessions. The WIV (and in some cases, visualization of the wound characterization values to be used in combination with the WIV) in the examples below were generated by applying adaptive threshold to the grayscale version of the wound activity map.

Ranking Map Image in Wound Management

One challenge in wound management, such as chronic wound management, is that the medical condition or nature of a wound can be viewed differently among clinicians. Current techniques may provide information about the wound's pathological history, but fail to provide reliable indicators of viability and/or restorative potential, e.g., whether wound and/or periwound is likely to develop complications, is capable of healing, or how healing progresses. Furthermore, wounds exist where no pathology is demonstrable by conventional diagnostic techniques. Various embodiments of the methods and systems described herein facilitate producing a consistent representation (not subjective to biases of perception) of the state of a particular tissue region (e.g., wound, periwound), and thus facilitate a more accurate subsequent assessment and formulation of care strategies (e.g., recommendation and assessment of efficacy care such as, for example, topical treatments, hyperbaric therapy; assessment of the tissue pre- and post-surgery; formulation of surgical strategy).

FIGS. 9A-9F illustrate applications of the ranking map image for assessment and management of wounds, such as for chronic non-healing wounds. The time series of fluorescence images (videos) were recorded with the aid of SPY® Elite fluorescence imaging device (available from NOVADAQ® Technologies Inc.). The time series of fluorescence images were then used in accordance with the various embodiments to generate the spatial maps of rank values, or ranking map images. In this example, the second variation of generating total rank value was applied as described above. The color image in FIG. 9A shows a wound observed during an initial assessment of the patient with the clinician prior to any therapy applied to the wound. FIG. 9B is a corresponding spatial map of rank values generated in accordance with the various embodiments. FIG. 9B clearly illustrates the medical condition of the wound and the periwound, namely that there is a region of elevated rank values in the wound (left arrow) surrounded by a region of suppressed rank values (right arrow). FIGS. 9C and 9E are color images taken during subsequent assessments of the wound following repeated episodes of treatment. FIGS. 9D and 9F are the ranking map images corresponding to FIGS. 9C and 9E, respectively. A clinician looking at FIG. 9C, which corresponds to the second assessment of the patient, may not get a clear indication of the efficacy of the particular treatment applied to the wound, as the appearance of the wound is generally similar to the wound in the initial visit prior to any treatment. In contrast, however, the corresponding ranking map image of FIG. 9D clearly shows the changing nature of the wound and a pattern of healing. Similarly, the ranking map image relating to a third assessment (FIG. 9F) clearly illustrates the progress of healing as indicated by the shrinking region (arrow) of elevated rank values when compared to the similar regions in FIGS. 9B and 9D at the earlier stages of treatment. Furthermore, the presence of such remaining elevated rank regions (which are believed to correlate with abnormal perfusion) was not apparent from the conventional visual appearance of the wound (FIG. 9E).

Ranking Map Image in Chest Surgery

Figure 10A:
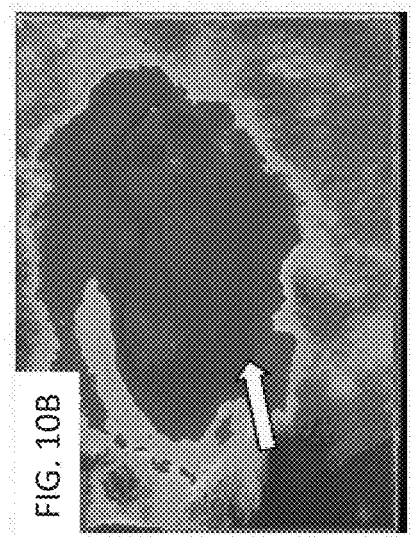
FIGS. 10A-10D depict exemplary images relating to an application of the methods and systems to chest surgery.
Figure 10B:
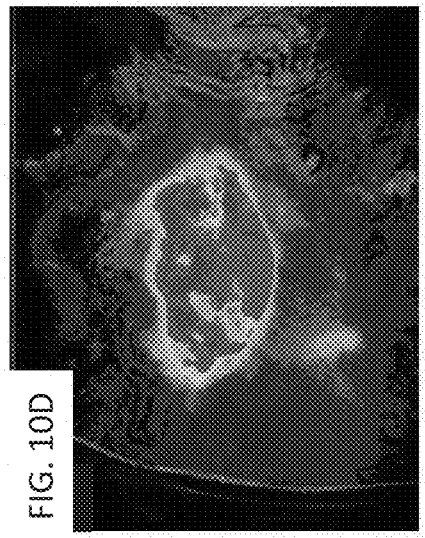
Figure 10C:
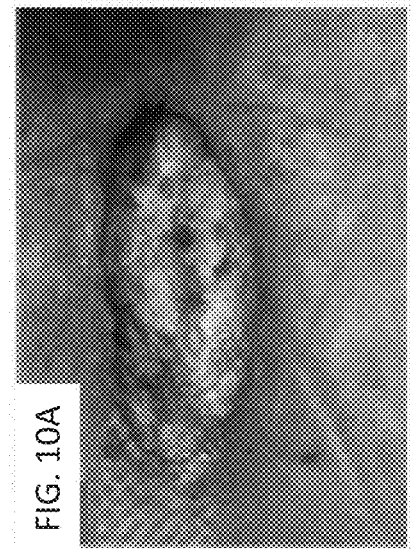
Figure 10D:
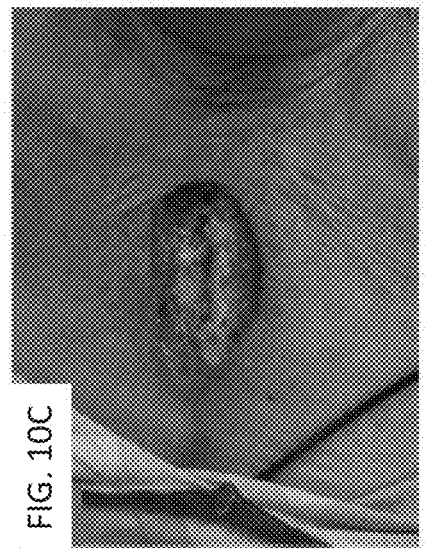

FIGS. 10A-10D illustrate how the ranking map image generated according to the various embodiments can be used to provide a visualization of tissue properties, in this case, in a surgical context for chest surgery. A time series of fluorescence angiography images (videos) was recorded during chest surgery with the aid of SPY® Elite fluorescence imaging device (available from NOVADAQ® Technologies Inc.), and was used in accordance with the various embodiments to generate a spatial map of rank values. In this example, algorithm in Formulas 1 and 2, as described above, was applied. FIG. 10A shows a color image of the chest wound after the surgery and the corresponding ranking map image in FIG. 10B. FIGS. 10C and 10D show a color image of the wound and the corresponding spatial map of rank values of the wound, respectively, after three weeks of hyperbaric oxygen treatment. As is illustrated by these figures, the abnormally bright area demonstrated around the wound in the spatial map of rank values (FIG. 10B, arrow) shrank and changed in appearance not only around the edges and in the periwound region but also internally (FIG. 10D) with treatment. The differences in the pattern of rank values are observed as compared to the initial wound in FIG. 10A, and indicate that the wound is healing. The spatial map of rank values generated in accordance with the various embodiments provides insights into the wound status, which the color image of the wound alone shown in FIG. 10C did not provide, thereby facilitating better wound care management and determination of any need for further surgical intervention.

Ranking Map Image in Reconstructive Surgery

Figure 11B:
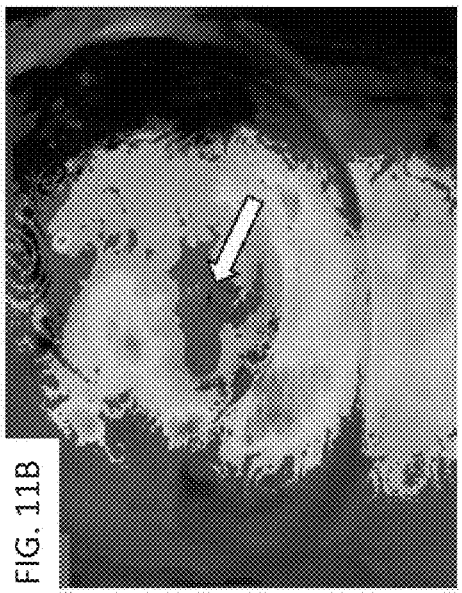
FIGS. 11A-11B depict exemplary images relating to an application of the methods and systems to reconstructive surgery.
Figure 11A:

FIGS. 11A-11B illustrate an application of the methods and systems according to the various embodiments to reconstructive breast surgery. Data was collected in the course of mastectomy surgeries performed on several patients. A time series of fluorescence angiography images (videos) were recorded with the aid of SPY® Elite fluorescence imaging device (available from NOVADAQ® Technologies Inc.), and this data was used to generate the spatial map of rank values. In this example, the algorithm in Formulas 1 and 2, as described above, was applied to generate total rank values. Three types of recordings were performed for each breast undergoing treatment: pre-incision baseline, post-mastectomy, and post-reconstruction. In addition, a color snapshot was taken a week after the procedures as means to evaluate the clinical outcome.

The ranking map image (FIG. 11B) has identified an area (indicated with an arrow) around the nipple in which the tissue was significantly different (compromised) as compared to the neighboring tissue. The area identified with the ranking map image showed reduced rank values for this tissue as compared to the surrounding tissue. A color snapshot of the breast from which the data was collected, taken one week after the surgery, showed necrosis around the nipple (FIG. 11A). The shape of necrosis is closely approximated by the abnormally colored area on the spatial map of rank values (arrow). Thus, the spatial map of rank values identified a problem in the tissue prior to identification of the problem by the clinician.

Case Examples of Wound Management Applications

Case 1—Traumatic Fracture Wound

FIGS. 12A to 12H illustrate an application of the method and system of the present invention for quantitative assessment and management of wounds, such as for example, a wound caused by a traumatic fracture. The patient was a 72 year oldmale who incurred a traumatic, compound bimalleolar fracture of his left ankle that required operative repair with an open reduction/internal-fixation procedure. The surgical site has become fully disrupted, threatening the fixation plates and hence the extremity. Hyperbaric oxygen therapy (HBOT) therapy was recommended.

The color image in FIG. 12A shows a wound observed during an initial assessment of the patient with the clinician prior to any therapy applied to the wound, and FIG. 12E is a color image of the wound one month after the initial assessment following repeated episodes of treatment. The maximum perfusion maps of the wound were generated as described above, an example of which is illustrated in FIG. 12B taken during a first assessment of the patient and FIG. 12F taken during a follow up visit one month after treatment and the initial assessment, were recorded with the aid of LUNA® fluorescence imaging system (available from NOVADAQ® Technologies Inc.) and using ICG as the fluorescence imaging agent. The wound activity maps and the wound index value (WIV) for the wound were generated as described above. FIGS. 12C and 12G illustrate the wound activity maps for the initial visit and at one month following the initial visit, respectively. FIGS. 12D and 12H illustrate or visualize the wound characterization values corresponding to the wound (i.e., segregated from the non-wound characterization values), generated from a comparison of each of the rank values with a reference value and processing as described above for the initial visit and one month following the initial visit, respectively. A healthy tissue region in the target tissue of the patient (shown in green in FIGS. 12C and 12G) was used to derive the reference value. FIGS. 12D and 12H further indicate the wound index value for the initial visit of the patient (WIV 50) and after one month (WIV 6), respectively.

FIG. 12C clearly illustrates the medical condition of the wound and the periwound, namely that there is a region of elevated rank values in the wound (e.g., red in FIG. 12C) surrounded by a region of lower rank values that are still distinct from the healthy tissue (yellow in FIG. 12C). FIG. 12D clearly indicates a large area of hyper perfusion in the wound, which is further quantified by the WIV of 50.

A clinician looking at FIG. 12E (taken at one month during subsequent assessment of the wound following repeated episodes of treatment) would get some visual indication that the wound has healed to some extent, but it would not be clear from this visual assessment whether treatment should be discontinued. In contrast, however, the corresponding wound activity map (FIG. 12G) visualizes the changing nature of the wound and a pattern of healing. This pattern is even more dramatically illustrated in the visualization of wound characterizations values (values relating to the wound only not diluted or skewed by non-wound values) in FIG. 12H, which show a drastic decrease in the wound related areas as compared to the initial visit (FIG. 12D). Similarly, quantification of the wound, which at 1 month is now at WIV 6 (a decrease from an initial value of WIV 50), indicates that the wound may have significantly healed and may be on its way to recovery, where the WIV will likely become 0. The decrease in WIV appears to correlate with the trimming down of the excessive blood vessels to the normal levels as was discussed above in connection with angiogenesis, wound healing and tissue regeneration.

Thus the wound index value, WIV, is may help to provide a quantitative indication of a state of the wound (e.g., severity, activity of the wound). The WIV provides for an objective, standardized protocol for assessing tissue blood flow and/or perfusion, which may facilitate a way to reliably and consistently compare and track blood flow and/or perfusion status of a patient over time across multiple imaging sessions, regardless of the clinician performing the assessment.

Case 2—Infected Wound

FIGS. 13A to 13K illustrate an application of the method and system of the present invention for quantitative assessment and management of wounds, such as for example, an infected wound. The patient was a 48 year old male with an infected wound in the left leg. Open-reduction-internal-fixation reconstruction procedure was performed. The wound has been open for several months. Refractory to aggressive topical wound care and antibiotics treatments were applied, and HBOT therapy was recommended. The methods described above in connection with image acquisition, processing and generation of the wound index value apply to this case.

Figure 13C:
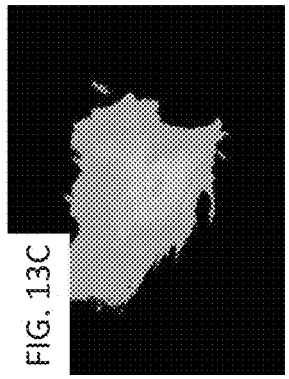
FIGS. 13A-13K depict exemplary images relating to an application of the methods and systems to wound management of an infected wound.
Figure 13E:
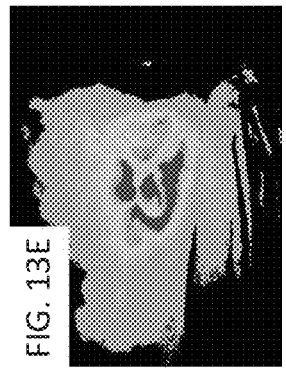
Figure 13H:
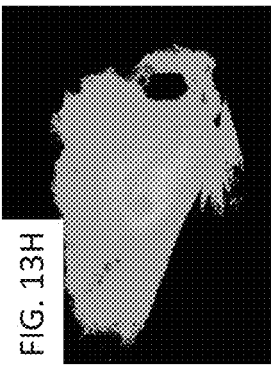
Figure 13K:
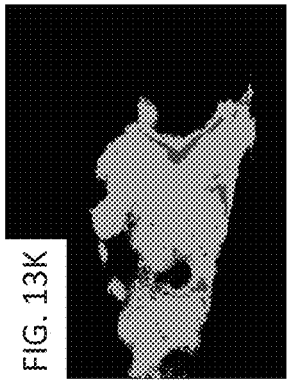
Figure 13B:
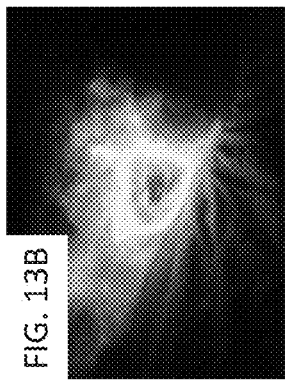
Figure 13D:
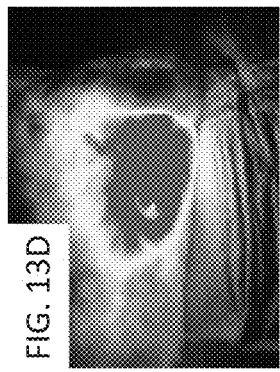
Figure 13G:
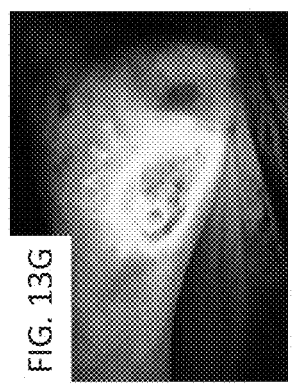
Figure 13J:
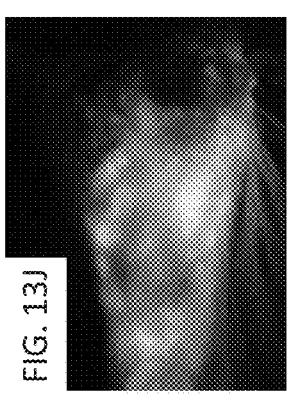
Figure 13A:
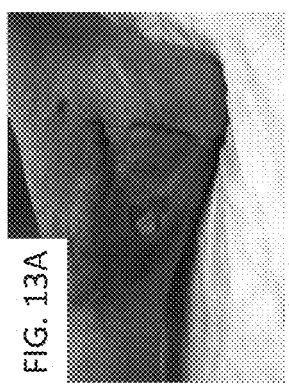
Figure 13F:
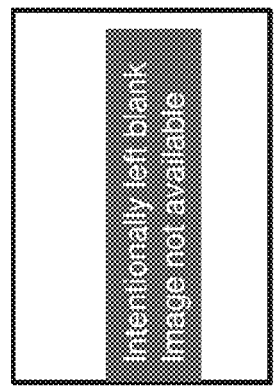
Figure 13F:
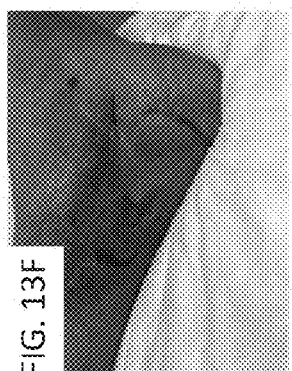
Figure 13I:
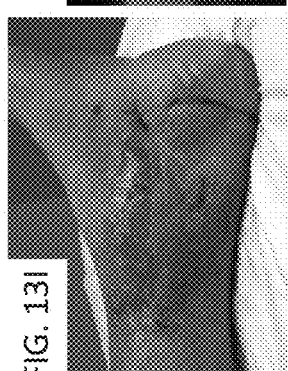

FIGS. 13A, 13F and 13I are color images of the wound during an initial assessment (FIG. 13A) and thereafter following treatment, which occurred at 2 weeks (no image available), 2 months (FIG. 13F), and 3 months (FIG. 13I) from the initial assessment. FIGS. 13B, 13D, 13G, and 13J are the corresponding maximum perfusion maps, and FIGS. 13C, 13E, 13H, and 13K are the corresponding wound activity maps. A healthy tissue region in the target tissue of the patient (shown in green in FIGS. 13C, 13E, 13H and 13K) was used to derive the reference value. In this example, in contrast to Case 1, the comparator data set was not visualized, but rather the wound index value (WIV) alone was generated as described above, and was used as the quantitative measure of the wound.

This case is also an example of the wound on its way to recovery. The increase in the WIV at 2 weeks (FIG. 13E) illustrates that inflammation occurred following the initial visit, and thus increased angiogenesis in the wound. The wound then began to heal as indicated by a decrease in the WIV at 2 months (FIG. 13H), which eventually became "0" at 3 months (FIG. 13K) indicating that the wound is healed. Thus the WIV values in this healing process appear to correlate with the angiogenesis curve and healing, and quantify the various stages of the healing process. Furthermore, the information obtained from the WIV, alone or in combination with the wound activity map, would not have been available to the clinician using conventional visual examination of the wound.

Case 3—Ischemic Wound

FIGS. 14A to 14I illustrate an application of the method and system of the present invention for quantitative assessment and management of wounds, such as for example, an ischemic wound. The patient was 51 year old male with left foot ischemic wound with an amputated metatarsal with osteomyelitis and ascending fasciitis, and obliterative end arteritis. Refractory to aggressive topical care and antibiotics treatments have been applied. HBOT was recommended and started. The methods described above in connection with image acquisition, processing and generation of the wound index value apply to this case.

Figure 14C:
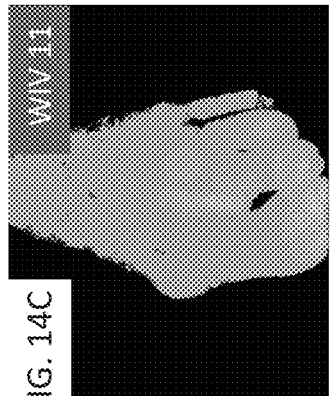
FIGS. 14A-14I depict exemplary images relating to an application of the methods and systems to wound management of an ischemic wound.
Figure 14F:
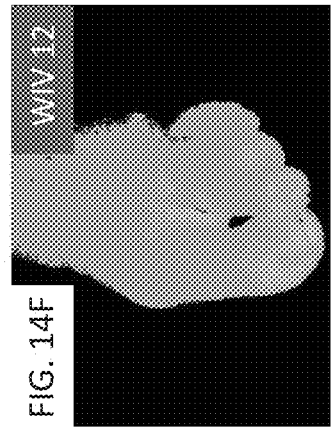
Figure 14I:
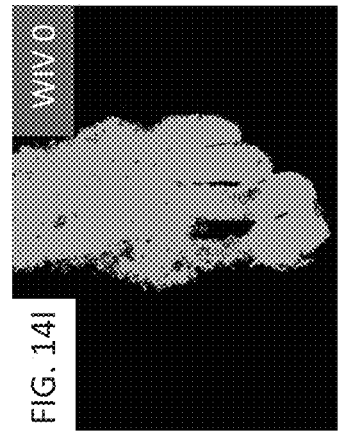
Figure 14B:
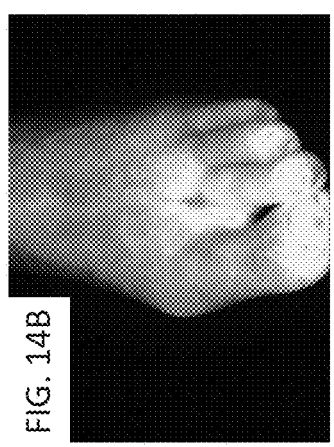
Figure 14E:
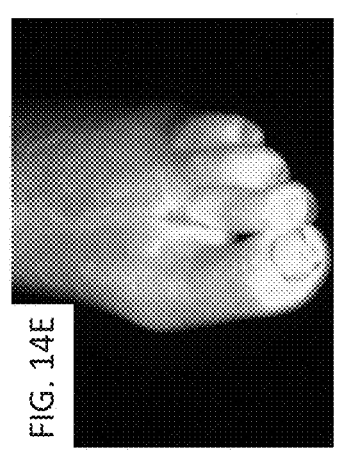
Figure 14H:
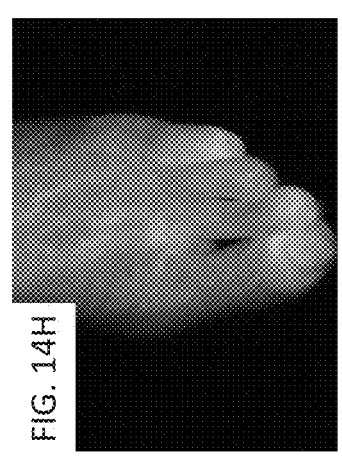
Figure 14A:
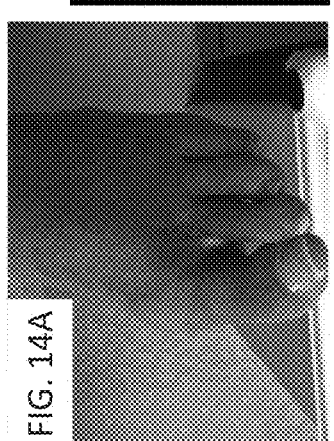
Figure 14D:
Figure 14G:

FIGS. 14A, 14D and 14G are color images of the wound during an initial assessment and thereafter following treatment which occurred at 5 days (FIG. 14D) and 1 month (FIG. 14G) following the initial assessment. FIGS. 14B, 14E, and 14H are the corresponding maximum perfusion maps, and FIGS. 14C, 14F, and 14I are the corresponding wound activity maps. A healthy tissue region in the target tissue of the patient (shown in green in FIGS. 14C, 14F, and 14I) was used to derive the reference value. In this example, the comparator data set was not visualized, in contrast to Case 1, but rather the WIV alone was generated as described above, and was used as the quantitative measure of the wound for the wound.

The difference in the WIV at 5 days (FIG. 14C) and at 1 month (FIG. 14F) following treatment is not statistically significant because the toe region was cut off during imaging at 5 days. Nevertheless, the WIV decreases with time, indicating that the wound has healed, which would not have been apparent from conventional visual examination alone.

Case 4—Reconstructive Surgery Application

FIGS. 15A-15L provide an example illustrating application of the methods and systems to reconstructive surgery such as, for example, breast reconstructive surgery. The patient was a 46 year old female who underwent bilateral mastectomies with immediate reconstruction. 48 hours postoperatively, she was deemed to have ischemic compromise of the inferior pole of the right breast. HBOT therapy was recommended. The methods described above in connection with image acquisition (recorded with the aid of SPY® fluorescence imaging system available from NOVADAQ® Technologies Inc.), processing and generation of the wound index value apply to this case.

FIGS. 15A, 15E and 15I are color images of the wound during an initial assessment (FIG. 15A) and thereafter following treatment which were taken at 1 week (FIG. 15E) and 3 weeks (FIG. 15I) after the initial assessment. FIGS. 15B, 15F, and 15J are the corresponding maximum perfusion maps, and FIGS. 15C, 15G, and 15K are the corresponding wound activity maps.

FIGS. 15D, 15H, and 15L visualize the wound characterization values corresponding to the wound (i.e., segregated from the non-wound characterization values), generated from a comparison of each of the rank values in with a reference value and processing as described above for the initial visit and follow up visits. A healthy tissue region in the target tissue of the patient (shown in green in FIGS. 15C, 15G, and 15K) was used to derive the reference value. From this data, the wound index value (WIV) was generated (FIGS. 15D, 15H, and 15L) for the initial visit and thereafter. This case demonstrates the healing of a hypo-perfused wound. The increase in WIV correlates with the increased activity of the blood vessel formation as discussed in connection with angiogenesis. HBOT therapy has triggered the process of angiogenesis that resulted first in increased blood flow activity around the hypo-perfused area of the tissue (FIGS. 15F, 15G, and 15H). As the healing progresses, the increased flow spreads inside the wound thus resulting in higher values of the wound index (FIGS. 15J, 15K, and 15L).

Additional Variations

Generally, in one variation, a computer-implemented method comprises generating a time-intensity curve for a calculation region in a time series of angiography images of tissue of a subject, calculating a rank value for the calculation region based on a plurality of parameters selected to approximate the time-intensity curve, and generating a spatial map of the calculated rank values. In some variations, the time series of angiography images comprises a time series of fluorescence angiography images. In some variations, the spatial map of the calculated rank values represents temporal characteristics of emitted fluorescence as a bolus of a fluorescence imaging agent moves through the tissue. In some variations, the spatial map of the calculated rank values represents a property of the tissue, a condition of the tissue, or a combination thereof. In some variations, the spatial map of the calculated rank values represents healing status of the tissue. In some variations, the property of the tissue or the condition of the tissue comprises inflammation, malignancy, abnormality, disease, or a combination thereof.

In some variations, the fluorescence imaging agent comprises a fluorescence dye, an analogue thereof, a derivative thereof, or a combination thereof. In some variations, the fluorescence dye comprises a tricarbocyanine dye. In some variations, the fluorescence dye comprises indocyanine green (ICG), fluorescein isothiocyanate, rhodamine, phycoerythrin, phycocyanin, allophycocyanin, o-phthaldehyde, fluorescamine, rose Bengal, trypan blue, fluoro-gold, or a combination thereof. In some variations, the fluorescence imaging agent is administered to the subject immediately prior to acquisition of the time series of fluorescence angiography images.

In some variations, a parameter in the plurality of parameters comprises duration of a region of increasing intensity of the time-intensity curve, intensity change within a region of increasing intensity of the time-intensity curve intensity change within a region of increasing intensity of the time-intensity curve, duration of a region of peak intensity of the time-intensity curve, intensity change within a region of peak intensity of the time-intensity curve, duration of a region of decreasing intensity of the time-intensity curve, or intensity change within a region of decreasing intensity of the time-intensity curve. In some variations, a parameter in the plurality of parameters comprises duration of a perfusion onset phase of the time-intensity curve, intensity change within a perfusion onset phase of the time-intensity curve, duration of an arterial phase of the time-intensity curve, intensity change within an arterial phase of the time-intensity curve, duration of a micro-vascular phase of the time-intensity curve, intensity change within a micro-vascular phase of the time-intensity curve, duration of a venous phase of the time-intensity curve, or intensity change within a venous phase of the time-intensity curve. In some variations, each parameter in the plurality of parameters is a numerical curve-fitting algorithm. In some variations, approximation of the time-intensity curve comprises approximation of a portion of the time-intensity curve.

In some variations, the time series of angiography images comprises a plurality of individual image frames ordered consecutively by acquisition time. In some variations, the individual image frames are spatially aligned. In some variations, the time series of angiography images is pre-processed to extract selected data, calculate a baseline intensity, perform an image quality validation process, or a combination thereof. In some variations, the calculation region comprises an individual pixel or a group of individual pixels.

In some variations, generating the spatial map of the calculated rank values comprises assigning an intensity value to each calculated rank value for a plurality of calculation regions. In some variations, the calculated rank value and the intensity value are in a direct relationship.

In some variations, the method comprises superimposing the spatial map of the calculated rank values on an anatomical image of the tissue of the subject. In some variations, the method comprises acquiring the time series of angiography images of the tissue of the subject. In some variations, the time series of angiography images is a time series of fluorescence angiography images.

In some variations, the acquisition is performed using a fluorescence imaging system. In some of these variations, the fluorescence imaging system comprises use of a fluorescence imaging agent. In some variations, the fluorescence imaging agent comprises a fluorescence dye, an analogue thereof, a derivative thereof, or a combination thereof. In some variations, the fluorescence dye comprises a tricarbocyanine dye. In some variations, the fluorescence dye comprises indocyanine green (ICG), fluorescein isothiocyanate, rhodamine, phycoerythrin, phycocyanin, allophycocyanin, o-phthaldehyde, fluorescamine, rose Bengal, trypan blue, fluoro-gold, or a combination thereof. In some variations, the fluorescence imaging agent is administered to the subject immediately prior to the acquisition of the time series of fluorescence angiography images.

Generally, in one variation, there is disclosed a computer-implemented method operating with a fluorescence imaging system, the fluorescence imaging system comprising: a light source configured to illuminate tissue of a subject to induce fluorescence emission from a fluorescence agent in the tissue of the subject; an image acquisition assembly configured to acquire a time series of fluorescence angiography images from the fluorescence emission; and a processor assembly configured to process the time series of fluorescence angiography images. In these variations, the method comprises: generating, via the processor, a time-intensity curve for a calculation region in the time series of fluorescence angiography images; calculating, via the processor, a rank value for the calculation region based on a plurality of parameters selected to approximate the time-intensity curve; and generating, via the processor, a spatial map of the calculated rank values.

In some variations, the light source of the fluorescence imaging system comprises an illumination module comprising a fluorescence excitation source configured to generate an excitation light. In some variations, the illumination module further comprises an optical element configured to shape and guide the excitation light exiting the illumination module. In some variations, the optical element comprises a lens, a light guide, a diffuser, or a combination thereof. In some variations, the fluorescence imaging system further comprises optical elements disposed in front of the image acquisition assembly configured to capture, filter, and direct the fluorescence emission produced by the fluorescence imaging agent to the image sensor assembly.

Generally, in one variation, a system for processing a time series of angiography images of tissue of a subject comprises a user interface; a processor configured to communicate with the user interface; a non-transitory computer-readable storage medium having instructions stored which, when executed by the processor, cause the processor to perform operations comprising: generating a time-intensity curve for a calculation region in the time series of angiography images of the tissue of the subject; calculating a rank value for the calculation region based on a plurality of parameters selected to approximate the time-intensity curve; and generating a spatial map of the calculated rank values.

In some variations, the processor is in communication with an imaging system. In some variations, the system comprises an imaging system. In some variations, the processor is a component of the imaging system. In some variations, the processor is configured to control an operation of the imaging system. In some variations, the imaging system is a fluorescence imaging system and the time series of angiography images is a time series of fluorescence angiography images. In some of variations, the fluorescence imaging system comprises: an illumination module configured to illuminate the tissue of the subject to induce fluorescence emission from a fluorescence imaging agent in the tissue of the subject; and a camera assembly configured to acquire the time series of fluorescence angiography images.

Generally, in one variation, a non-transitory tangible computer-readable medium has computer-executable program code means embedded thereon comprising a method for processing of a time series of angiography images of tissue of a subject. The method comprises generating a time-intensity curve for a calculation region in the time series of angiography images; calculating a rank value for the calculation region based on a plurality of parameters selected to approximate the time-intensity curve; and generating a spatial map of the calculated rank values.

Generally, in one variation, a kit for processing a time series of angiography images of tissue of a subject includes the system of any of the variations described herein and a fluorescence imaging agent.

Generally, in one variation, there is disclosed a fluorescence imaging agent for use in a computer-implemented method, the method comprising: generating a time-intensity curve for a calculation region in a time series of angiography images of tissue of a subject; calculating a rank value for the calculation region based on a plurality of parameters selected to approximate the time-intensity curve; and generating a spatial map of the calculated rank values. In some variations, there is disclosed a fluorescence imaging agent for use in any the methods and systems described herein for wound management. In some of these variations, the wound management comprises chronic wound management. In some variations, the fluorescence imaging agent comprises ICG.

Generally, in one variation, a computer-implemented method of quantitatively assessing a wound in a target tissue of a subject comprises generating a time-intensity curve for a calculation region in a time series of input data obtained from the target tissue, the time series of input data capturing transit of an imaging agent through the target tissue; assigning a rank value for the calculation region based on a parameter selected to approximate the time-intensity curve; generating a data set based on a comparison of each of the rank values with a reference value; and processing the data set to generate a wound index value for the wound. In some variations, the index value generated is used in a machine learning process.

In some variations, the data set comprises first and second data sets. In some variations, the method comprises applying a modulation function to each the first and second data sets. In some variations, applying the modulation function to each the first and second data sets comprises: applying a first modulation function the first data set to generate a first modulated data set; and applying a second modulation function, distinct from the first modulation function, to the second data set to generate a second modulated data set. In some variations, the first modulated data set comprises a plurality of wound characterization values, and the second modulated data set comprises a plurality of non-wound characterization values. In some variations, the first modulation function is an identity function. In some variations, the second modulation function causes the second modulated data set to equal zero.

In some variations, the processing the data set to generate the wound index value representing the state of the wound comprises processing the wound characterization values using the non-wound characterization values. In some variations, processing the wound characterization values using the non-wound characterization values to generate the wound index value comprises adding up all the rank values in the first data set and dividing by a total number of pixels in the calculation region. In some variations, processing the data set to generate the wound index value comprises adding up all the rank values in the first data set and dividing by a total number of pixels representing a tissue portion in the calculation region while excluding background.

In some variations, the method comprises visualizing a plurality of the rank values, the data in the data set, a plurality of the wound index values, or a combination thereof. In some variations, visualizing the plurality of the rank values, the data in the data set, or a combination thereof comprises generating a spatial map. In some variations, the method comprises superimposing the spatial map over an anatomical image of the target tissue. In some variations, visualizing the plurality of the wound index values comprises tracking the wound index value over time. In some variations, tracking the wound index value over time comprises generating a graph representation of a change in the wound index value over time. In some variations, the change in the wound index value over time represents a change in a state of the wound over time.

In some variations, the reference value is modified by a modifier. In some variations, the modifier comprises a tolerance value, a multiplier, averaging of multiple reference values, or a combination thereof. In some variations, the reference value is obtained by generating a reference time-intensity curve for a reference calculation region in a time series of reference input data obtained from a reference tissue, the time series of reference input data capturing transit of an imaging agent through the reference tissue; and calculating a reference rank value for the reference calculation region based on a parameter selected to approximate the reference time-intensity curve. In some variations, the reference tissue is tissue of a healthy subject, a population of healthy subjects, a healthy tissue region in the target tissue of the subject, a healthy tissue region outside the target tissue of the subject.

In some variations, the wound comprises an injury to the target tissue. In some variations, the injury comprises a surgical wound, a chronic wound, an acute wound. In some variations, the surgical wound, the chronic wound, or the acute wound comprises an incision, a pressure ulcer, a laceration, an abrasion, a puncture, a contusion, an avulsion, a cavity, a burn, or a combination thereof. In some variations, the chronic wound comprises a pressure ulcer, a venous ulcer, an arterial ulcer, a diabetic lower extremity ulcer, or a combination thereof. In some variations, the wound comprises a deviation from the reference value. In some variations, the state of the wound comprises a property of the wound, a condition of the wound, a healing status of the wound, or a combination thereof. In some variations, the property of the wound, the condition of the wound, or the healing status of the wound comprises inflammation, malignancy, abnormality, disease, or a combination thereof.

In some variations, the time series of input data comprises a time series of fluorescence input data. In some variations, the method comprises acquiring the time series of fluorescence input data during fluorescence imaging using a fluorescence imaging system, wherein the imaging agent is a fluorescence imaging agent. In some variations, the fluorescence imaging agent is administered to the subject immediately prior to acquisition of the time series of fluorescence input data. In some variations, the fluorescence imaging agent comprises a fluorescence dye, an analogue thereof, a derivative thereof, or a combination thereof. In some variations, the fluorescence dye comprises a tricarbocyanine dye. In some variations, the tricarbocyanine dye is indocyanine green (ICG). In some variations, the fluorescence dye comprises ICG, fluorescein isothiocyanate, rhodamine, phycoerythrin, phycocyanin, allophycocyanin, o-phthaldehyde, fluorescamine, rose Bengal, trypan blue, fluoro-gold, or a combination thereof.

In some variations, the parameter selected to approximate the time-intensity curve comprises duration of a region of increasing intensity of the time-intensity curve, intensity change within a region of increasing intensity of the time-intensity curve intensity change within a region of increasing intensity of the time-intensity curve, duration of a region of peak intensity of the time-intensity curve, intensity change within a region of peak intensity of the time-intensity curve, duration of a region of decreasing intensity of the time-intensity curve, or intensity change within a region of decreasing intensity of the time-intensity curve, or a combination thereof. In some variations, the parameter selected to approximate the time-intensity curve comprises duration of a perfusion onset phase of the time-intensity curve, intensity change within a perfusion onset phase of the time-intensity curve, duration of an arterial phase of the time-intensity curve, intensity change within an arterial phase of the time-intensity curve, duration of a micro-vascular phase of the time-intensity curve, intensity change within a micro-vascular phase of the time-intensity curve, duration of a venous phase of the time-intensity curve, or intensity change within a venous phase of the time-intensity curve, or a combination thereof. In some variations, the parameter selected to approximate the time-intensity curve is a numerical curve-fitting algorithm. In some variations, the approximation of the time-intensity curve comprises approximation of a portion of the time-intensity curve.

In some variations, the time series of input data comprises a plurality of individual image frames ordered consecutively by acquisition time. In some variations, the individual image frames are spatially aligned. In some variations, the time series of input data is pre-processed to extract selected data, calculate a baseline intensity, perform an image quality validation process, or a combination thereof. In some variations, the calculation region comprises an individual pixel or a group of individual pixels.

In some variations, comprising tracking the wound index value to assess progress of healing, treatment, or a combination thereof. In some variations, the wound index value further represents a quantitative profile of the wound.

In some variations, the wound index value in any of the variations descried herein may be used in combination with the visualization in any of the manners described herein for assessing the wound at a selected point in time or over time, and/or for assessing blood flow, tissue perfusion, or a combination thereof in the wound.

Generally, in one variation, a computer-implemented method of quantitatively assessing a wound in a target tissue of a subject comprises administering a fluorescence agent into the bloodstream of the subject; illuminating the target tissue of the subject to excite the fluorescence agent in the blood in the target tissue; acquiring a time series of fluorescence input data arising from the emission, the time series of fluorescence input data capturing transit of the fluorescence agent through the target tissue; generating a time-intensity curve for a calculation region in the time series of fluorescence input data; calculating a rank value for the calculation region based on a parameter selected to approximate the time-intensity curve; generating a data set based on a comparison of each of the rank values with a reference value; and processing the data set to generate a wound index value for the wound.

Generally, in one computer-implemented method operating with a fluorescence imaging system, the fluorescence imaging system comprises a light source configured to illuminate tissue of a subject to induce fluorescence emission from a fluorescence agent in the tissue of the subject; an image acquisition assembly configured to acquire a time series of fluorescence input data from the fluorescence emission; and a processor assembly configured to process the time series of fluorescence input data. The method comprises: generating, via the processor, a time-intensity curve for a calculation region in the time series of fluorescence input data obtained from the target tissue, the time series of fluorescence input data capturing transit of the fluorescence agent through the target tissue; assigning, via the processor, a rank value for the calculation region based on a parameter selected to approximate the time-intensity curve; generating, via the processor, a data set based on a comparison of each of the rank values with a reference value; and processing, via the processor, the data set to generate a wound index value for the wound. In some variations, the light source of the fluorescence imaging system comprises an illumination module comprising a fluorescence excitation source configured to generate an excitation light. In some variations, the illumination module further comprises an optical element configured to shape and guide the excitation light exiting the illumination module. In some variations, the optical element comprises a lens, a light guide, a diffuser, or a combination thereof. In some variations, the fluorescence imaging system comprises optical elements disposed in front of the image acquisition assembly configured to capture, filter, and direct the fluorescence emission produced by the fluorescence imaging agent to the image sensor assembly.

Generally, in one variations, a system for quantitatively assessing a wound in a target tissue of a subject comprises a user interface; a processor configured to communicate with the user interface; a non-transitory computer-readable storage medium having instructions stored which, when executed by the processor, cause the processor to perform operations comprising: generating a time-intensity curve for a calculation region in the time series of fluorescence images of the target tissue; assigning a rank value for the calculation region based on a parameter selected to approximate the time-intensity curve; generating a data set based on a comparison of each of the rank values with a reference value; and processing the data set to generate a wound index value for the wound.

In some variations, the processor is in communication with a fluorescence imaging system. In some variations, the system further comprises a fluorescence imaging system. In some variations, the processor is a component of the fluorescence imaging system. In some variations, the processor is configured to control an operation of the fluorescence imaging system. In some variations, the fluorescence imaging system comprises: an illumination module configured to illuminate the tissue of the subject to induce fluorescence emission from a fluorescence imaging agent in the tissue of the subject; and a camera assembly configured to acquire the time series of fluorescence images.

Generally, in one variation, a non-transitory tangible computer-readable medium has computer-executable program code means embedded thereon comprising a method of quantitatively assessing a wound in a target tissue of a subject. The method comprises generating a time-intensity curve for a calculation region in a time series of fluorescence input data obtained from the target tissue, the time series of fluorescence input data capturing transit of a fluorescence imaging agent through the target tissue; assigning a rank value for the calculation region based on a parameter selected to approximate the time-intensity curve; generating a data set based on a comparison of each of the rank values with a reference value; and processing the data set to generate a wound index value for the wound.

Generally, in one variation, a kit for quantitatively assessing a wound in a target tissue of a subject includes the system of any of the variations described herein and a fluorescence imaging agent.

Generally, in one variation, there is disclosed a fluorescence imaging agent for use in a computer-implemented method of quantitatively assessing a wound in a target tissue of a subject, the method comprising: generating a time-intensity curve for a calculation region in a time series of fluorescence input data obtained from the target tissue, the time series of fluorescence input data capturing transit of the fluorescence imaging agent through the target tissue; assigning a rank value for the calculation region based on a parameter selected to approximate the time-intensity curve; generating a data set based on a comparison of each of the rank values with a reference value; and processing the data set to generate a wound index value for the wound. In some variations, there is disclosed a fluorescence imaging agent for use in any the methods and systems described herein for wound management. In some of these variations, the wound management comprises chronic wound management. In some variations, the fluorescence imaging agent comprises ICG.

Generally, in one variation, a computer-implemented method of quantitatively assessing a wound in a target tissue of a subject comprises: generating a time-intensity curve for a calculation region in a time series of input data obtained from the target tissue; assigning a rank value for the calculation region based on a parameter selected to approximate the time-intensity curve; generating a data set based on a comparison of each of the rank values with a reference value; and processing the data set to generate a wound index value of the wound.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments; however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A system for characterizing tissue of a subject, comprising:
   one or more processors; and
   memory having instructions stored thereon, the instructions, when executed by the one or more processors, cause the system to:
     receive a time series of fluorescence images of the tissue of the subject, wherein the images define a plurality of calculation regions;
     generate a plurality of time-intensity curves for the plurality of calculation regions;
     generate, based on the plurality of time-intensity curves for the plurality of calculation regions, a ranking map image representing the plurality of calculation regions, wherein the ranking map image comprises at least one spatial dimension, and wherein the at least one spatial dimension comprises a horizontal spatial dimension and a vertical spatial dimension.

2. The system of claim 1, wherein generating the ranking map image comprises:
   creating a plurality of sets of parameter values for the plurality of calculation regions, wherein the parameter values approximate at least a portion of the time-intensity curve; and
   generating the ranking map based on the set of parameter values for each calculation region.

3. The system of claim 2, wherein at least one parameter value in the plurality of sets of parameter values is related to time properties of the time-intensity curve, magnitude of intensity changes in the time-intensity curve, a coefficient relating to a polynomial characterization of the time-intensity curve, or a combination thereof.

4. The system of claim 2, wherein at least one parameter value in the plurality of sets of parameter values is for a parameter type comprising: (i) duration of a region of increasing intensity of the time-intensity curve, (ii) duration of a region of high intensity of the time-intensity curve, (iii) duration of a region of a plateau of the time-intensity curve, (iv) duration of a region of decreasing intensity of the time-intensity curve, or (v) a combination thereof.

5. The system of claim 2, wherein at least one parameter value in the plurality of sets of parameter values is for a parameter type comprising: (i) duration of a perfusion onset phase of the time-intensity curve, (ii) duration of an arterial phase of the time-intensity curve, (iii) duration of a micro-vascular phase of the time-intensity curve, (iv) duration of a venous phase of the time-intensity curve, or (v) a combination thereof.

6. The system of claim 2, wherein at least one parameter value in the plurality of sets of parameter values is for a parameter type comprising: (i) time to the onset of increasing fluorescence intensity, (ii) time for rapid or most rapid fluorescence intensity increase, (iii) time for rapid or most rapid fluorescence intensity decrease, (iv) rate of change in fluorescence intensity for any of the above-described regions of the time-intensity curve, or (v) a combination thereof.

7. The system of claim 2, wherein at least one parameter value in the plurality of sets of parameter values is for a parameter type comprising: (i) intensity change within a region of increasing intensity of the time-intensity curve, (ii) intensity change within a region of high intensity of the time-intensity curve, (iii) intensity change within a region of decreasing intensity of the time-intensity curve, or (iv) a combination thereof.

8. The system of claim 2, wherein at least one parameter value in the plurality of sets of parameter values is for a parameter type comprising: (i) intensity change during a perfusion onset phase of the time-intensity curve, (ii) intensity change during an arterial phase of the time-intensity curve, (iii) intensity change during a micro-vascular phase of the time-intensity curve, (iv) intensity change during a venous phase of the time-intensity curve, or a combination thereof.

9. The system of claim 2, wherein at least one parameter value in the plurality of sets of parameter values is for a parameter type comprising: (i) intensity change during a period of rapid or most rapid fluorescence intensity increase, and (ii) intensity change during a period of rapid or most rapid fluorescence intensity decrease.

10. The system of claim 2, wherein generating the ranking map image further comprises:

generating a total rank value for each calculation region by comparing the plurality of sets of parameter values for the plurality of calculation regions; and converting the total rank values for the calculation regions into the ranking map image.

11. The system of claim 10, wherein each parameter value is a value for a parameter type, and wherein comparing the plurality of sets of parameter values comprises generating a set of numeric ranks for the parameter types for each calculation region.

12. The system of claim 11, wherein generating a total rank value for each calculation region comprises summing the set of numeric ranks for each calculation region.

13. The system of claim 11, wherein generating a total rank value for each calculation region comprises mapping the set of numeric metrics for each calculation region with a hash function.

14. The system of claim 13, wherein the hash function comprises a cyclic redundancy check or a pairing function.

15. The system of claim 10, wherein converting the total rank values into the ranking map image comprises correlating each total rank value to an intensity value.

16. The system of claim 10, wherein converting the total rank values into the ranking map image comprises correlating each total rank value to (i) an intensity value or (ii) a grayscale or color display value.

17. The system of claim 1, wherein at least one calculation region is defined by one pixel or one voxel.

18. The system of claim 1, wherein the instructions cause the system to superimpose the ranking map image on an anatomical image of the tissue on the display.

19. The system of claim 1, further comprising a display, wherein the instructions cause the system to display the ranking map image on the display.

20. The system of claim 1, further comprising a light source configured to provide an excitation light to induce fluorescence emission from a fluorescence imaging agent in the tissue.

21. The system of claim 1, further comprising an image acquisition assembly that generates the time series of fluorescence images based on fluorescence emission from a fluorescence imaging agent in the tissue.

22. The system of claim 1, wherein receiving a time series of fluorescence images comprises capturing transit of a bolus of a fluorescence imaging agent moving through the tissue.

23. The system of claim 22, wherein the fluorescence imaging agent comprises indocyanine green, fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof.

24. A method for use in medical imaging for characterizing tissue of a subject, the method comprising:
at a computer system including one or more processors and memory:
receiving a time series of fluorescence images of the tissue of the subject, wherein the images define a plurality of calculation regions;
generating a plurality of time-intensity curves for the plurality of calculation regions;
generating, based on the plurality of time-intensity curves for the plurality of calculation regions, a ranking map image representing the plurality of calculation regions, wherein the ranking map image comprises at least one spatial dimension, and wherein the at least one spatial dimension comprises a horizontal spatial dimension and a vertical spatial dimension.

* * * * *